(12) United States Patent
Bassaganya-Riera et al.

(10) Patent No.: US 9,119,881 B2
(45) Date of Patent: Sep. 1, 2015

(54) METHOD OF SYNERGISTICALLY ENHANCING THE THERAPEUTIC EFFICACY AND SAFETY OF MEDICATION THROUGH A COMBINATION THERAPY

(71) Applicant: Virginia Tech Intellectual Properties, Inc., Blacksburg, VA (US)

(72) Inventors: Josep Bassaganya-Riera, Blacksburg, VA (US); Amir J. Guri, Blacksburg, VA (US); Raquel Hontecillas, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 13/905,888

(22) Filed: May 30, 2013

(65) Prior Publication Data
US 2013/0261092 A1 Oct. 3, 2013

Related U.S. Application Data

(62) Division of application No. 12/695,915, filed on Jan. 28, 2010, now abandoned.

(51) Int. Cl.

| | | |
|---|---|---|
| A61K 31/19 | (2006.01) | |
| A61K 31/426 | (2006.01) | |
| A61K 31/4439 | (2006.01) | |
| A61K 47/12 | (2006.01) | |
| A61K 31/425 | (2006.01) | |
| A61K 31/4427 | (2006.01) | |
| A23L 1/30 | (2006.01) | |
| A61K 45/06 | (2006.01) | |

(52) U.S. Cl.
CPC .............. *A61K 47/12* (2013.01); *A23L 1/3002* (2013.01); *A61K 31/19* (2013.01); *A61K 31/425* (2013.01); *A61K 31/426* (2013.01); *A61K 31/4427* (2013.01); *A61K 31/4439* (2013.01); *A61K 45/06* (2013.01)

(58) Field of Classification Search
CPC .. A61K 31/19; A61K 31/426; A61K 31/4439
See application file for complete search history.

(56) References Cited

PUBLICATIONS

Ogden CL, Carroll MD, Curtin LR, McDowell MA, Tabak CJ, Flegal KM. Prevalence of overweight and obesity in the United States, 1999-2004. JAMA 2006;295:1549-55.
Clinical Guidelines on the Identification, Evaluation, and Treatment of Overweight and Obesity in Adults—The Evidence Report. National Institutes of Health. Obes Res 1998;6 Suppl 2:51S-209S.
Dietz WH. Health consequences of obesity in youth: childhood predictors of adult disease. Pediatrics 1998;101:518-25.
Hotamisligil GS. Role of endoplasmic reticulum stress and c-Jun NH2-terminal kinase pathways in inflammation and origin of obesity and diabetes. Diabetes 2005;54 Suppl 2:S73-8.
Tuncman G, Hirosumi J, Solinas G, Chang L, Karin M, Hotamisligil GS. Functional in vivo interactions between JNK1 and JNK2 isoforms in obesity and insulin resistance. Proc Natl Acad Sci U S A 2006;103:10741-6.
Yuan M, Konstantopoulos N, Lee J, et al. Reversal of obesity- and diet-induced insulin resistance with salicylates or targeted disruption of Ikkbeta. Science 2001;293:1673-7.
Arkan MC, Hevener AL, Greten FR, et al. IKK-beta links inflammation to obesityinduced insulin resistance. Nat Med 2005;11:191-8.
Davis JE, Gabler NK, Walker-Daniels J, Spurlock ME. Tlr-4 deficiency selectively protects against obesity induced by diets high in saturated fat. Obesity (Silver Spring) 2008;16:1248-55.
Lehmann JM, Moore LB, Smith-Oliver TA, Wilkison WO, Willson TM, Kliewer SA. An anti-diabetic thiazolidinedione is a high affinity ligand for peroxisome proliferator-activated receptor gamma (PPAR gamma). J Biol Chem 1995;270:12953-6.
Yamauchi T, Kadowaki T. [The molecular mechanisms by which PPAR gamma/RXR inhibitors improve insulin resistance]. Nippon Rinsho 2001;59:2245-54.
Bays HE, Gonzalez-Campoy JM, Bray GA, et al. Pathogenic potential of adipose tissue and metabolic consequences of adipocyte hypertrophy and increased visceral adiposity. Expert Rev Cardiovasc Ther 2008;6:343-68.
Weisberg SP, McCann D, Desai M, Rosenbaum M, Leibel RL, Ferrante AW, Jr. Obesity is associated with macrophage accumulation in adipose tissue. J Clin Invest 2003;112:1796-808.
Pascual G, Fong AL, Ogawa S, et al. A SUMOylation-dependent pathway mediates transrepression of inflammatory response genes by PPAR-gamma. Nature 2005;437:759-63.
Tanaka T, Fukunaga Y, Itoh H, et al. Therapeutic potential of thiazolidinediones in activation of peroxisome proliferator-activated receptor gamma for monocyte recruitment and endothelial regeneration. Eur J Pharmacol 2005;508:255-65.
Jennewein C, Kuhn AM, Schmidt MV, et al. Sumoylation of peroxisome proliferatoractivated receptor gamma by apoptotic cells prevents lipopolysaccharide-induced NCoR removal from kappaB binding sites mediating transrepression of proinflammatory cytokines. J Immunol 2008;181:5646-52.

(Continued)

*Primary Examiner* — Renee Claytor
(74) *Attorney, Agent, or Firm* — Blank Rome LLP

(57) ABSTRACT

The present invention provides combinations, for treatment of subjects suffering from or at high risk of developing diseases and disorders involving expression of peroxisome proliferator-activated receptors (PPAR). The combinations include abscisic acid and one other bioactive agent, which together provide synergistic effects toward treatment or blocking of development of the disease or disorder. In exemplary embodiments, a combination of abscisic acid and a thiazolidinedione (TZD) is provided for increased insulin sensitivity and improved (i.e., reduced) obesity-induced inflammation.

2 Claims, 8 Drawing Sheets

(56) References Cited

PUBLICATIONS

Blanquicett C, Roman J, Hart CM. Thiazolidinediones as anti-cancer agents. Cancer Ther 2008;6:25-34.

Mestre L, Docagne F, Correa F, et al. A cannabinoid agonist interferes with the progression of a chronic model of multiple sclerosis by downregulating adhesion molecules. Mol Cell Neurosci 2008.

Serghides L, Kain KC. Peroxisome proliferator-activated receptor gamma-retinoid X receptor agonists increase CD36—dependent phagocytosis of Plasmodium falciparum-parasitized erythrocytes and decrease malaria-induced TNF-alpha secretion by monocytes/macrophages. J Immunol 2001;166:6742-8.

Barna BP, Culver DA, Abraham S, et al. Depressed peroxisome proliferator-activated receptor gamma (PPargamma) is indicative of severe pulmonary sarcoidosis: possible involvement of interferon gamma (IFN-gamma). Sarcoidosis Vasc Diffuse Lung Dis 2006;23:93-100.

Serhan CN, Devchand PR. Novel anti-inflammatory targets for asthma. A role for PPARgamma? Am J Respir Cell Mol Biol 2001;24:658-61.

Diab A, Deng C, Smith JD, et al. Peroxisome proliferator-activated receptor-gamma agonist 15-deoxy-Delta(12,14)-prostaglandin J(2) ameliorates experimental autoimmune encephalomyelitis. J Immunol 2002;168:2508-15.

Diab A, Hussain RZ, Lovett-Racke AE, Chavis JA, Drew PD, Racke MK. Ligands for the peroxisome proliferator-activated receptor-gamma and the retinoid X receptor exert additive anti-inflammatory effects on experimental autoimmune encephalomyelitis. J Neuroimmunol 2004;148:116-26.

Raikwar HP, Muthian G, Rajasingh J, Johnson C, Bright JJ. PPARgamma antagonists exacerbate neural antigen-specific Th1 response and experimental allergic encephalomyelitis. J Neuroimmunol 2005;167:99-107.

Storer PD, Xu J, Chavis J, Drew PD. Peroxisome proliferator-activated receptor-gamma agonists inhibit the activation of microglia and astrocytes: implications for multiple sclerosis. J Neuroimmunol 2005;161:113-22.

Hontecillas R, Bassaganya-Riera J. Peroxisome proliferator-activated receptor gamma is required for regulatory CD4+ T cell-mediated protection against colitis. J Immunol 2007;178:2940-9.

Ramakers JD, Verstege MI, Thuijls G, Te Velde AA, Mensink RP, Plat J. The PPARgamma agonist rosiglitazone impairs colonic inflammation in mice with experimental colitis. J Clin Immunol 2007;27:275-83.

Lewis JD, Lichtenstein GR, Stein RB, et al. An open-label trial of the PPAR-gamma ligand rosiglitazone for active ulcerative colitis. Am J Gastroenterol 2001;96:3323-8.

Kobayashi T, Notoya K, Naito T, et al. Pioglitazone, a peroxisome proliferator-activated receptor gamma agonist, reduces the progression of experimental osteoarthritis in guinea pigs. Arthritis Rheum 2005;52:479-87.

Demerjian M, Man MQ, Choi EH, et al. Topical treatment with thiazolidinediones, activators of peroxisome proliferator-activated receptor-gamma, normalizes epidermal homeostasis in a murine hyperproliferative disease model. Exp Dermatol 2006;15:154-60.

Bolzano K. [Biguanides: reasons for withdrawal of drugs and remaining indications]. Acta Med Austriaca 1978;5:85-8.

d'Uscio LV, Baker TA, Mantilla CB, et al. Mechanism of endothelial dysfunction in apolipoprotein E-deficient mice. Arterioscler Thromb Vasc Biol 2001;21:1017-22.

Holst JJ. Treatment of type 2 diabetes mellitus with agonists of the GLP-1 receptor or DPP-IV inhibitors. Expert Opin Emerg Drugs 2004;9:155-66.

Drucker DJ, Philippe J, Mojsov S, Chick WL, Habener JF. Glucagon-like peptide I stimulates insulin gene expression and increases cyclic AMP levels in a rat islet cell line. Proc Natl Acad Sci U S A 1987;84:3434-8.

Klett C, Nobiling R, Gierschik P, Hackenthal E. Angiotensin II stimulates the synthesis of angiotensinogen in hepatocytes by inhibiting adenylylcyclase activity and stabilizing angiotensinogen mRNA. J Biol Chem 1993;268:25095-107.

Krumenacker JS, Katsuki S, Kots A, Murad F. Differential expression of genes involved in cGMP-dependent nitric oxide signaling in murine embryonic stem (ES) cells and ES cell derived cardiomyocytes. Nitric Oxide 2006;14:1-11.

Murad F. Shattuck Lecture. Nitric oxide and cyclic GMP in cell signaling and drug development. N Engl J Med 2006;355:2003-11.

Hanefeld M, Marx N, Pfutzner A, et al. Anti-inflammatory effects of pioglitazone and/or simvastatin in high cardiovascular risk patients with elevated high sensitivity C-reactive protein: the PIOSTAT Study. J Am Coll Cardiol 2007;49:290-7.

Martin G, Duez H, Blanquart C, et al. Statin-induced inhibition of the Rho-signaling pathway activates PPARalpha and induces HDL apoA-I. J Clin Invest 2001;107:1423-32.

Ye Y, Nishi SP, Manickavasagam S, et al. Activation of peroxisome proliferatoractivated receptor-gamma (PPAR-gamma) by atorvastatin is mediated by 15-deoxy-delta-12,14-PGJ2. Prostaglandins Other Lipid Mediat 2007;84:43-53.

Singh Ahuja H, Liu S, Crombie DL, et al. Differential effects of rexinoids and thiazolidinediones on metabolic gene expression in diabetic rodents. Mol Pharmacol 2001;59:765-73.

Altucci L, Rossin A, Hirsch O, et al. Rexinoid-triggered differentiation and tumorselective apoptosis of acute myeloid leukemia by protein kinase A-mediated desubordination of retinoid X receptor. Cancer Res 2005;65:8754-65.

Dragnev KH, Petty WJ, Ma Y, Rigas JR, Dmitrovsky E. Nonclassical retinoids and lung carcinogenesis. Clin Lung Cancer 2005;6:237-44.

Finkelstein EA, Trogdon JG, Cohen JW, Dietz W. Annual medical spending attributable to obesity: Payer- and service-specific estimates. Health Aff (Millwood) 2009.

Guri AJ, Hontecillas R, Si H, Liu D, Bassaganya-Riera 1. Dietary abscisic acid ameliorates glucose tolerance and obesity-related inflammation in db/db mice fed high-fat diets. Clin Nutr 2007;26:107-16.

Bruzzone S, Moreschi I, Usai C, et al. Abscisic acid is an endogenous cytokine in human granulocytes with cyclic adp-ribose as second messenger. Proc Natl Acad Sci USA 2007;104:5759-64.

Guri AJ, Hontecillas R, Ferrer G, et al. Loss ofppar gamma in immune cells impairs the ability of abscisic acid to improve insulin sensitivity by suppressing monocyte chemoattractant protein-I expression and macrophage infiltration into white adipose tissue. J Nutr Biochem 2008;19:216-28.

Marcy TR, Britton ML, Blevins SM. Second-generation thiazolidinediones and hepatotoxicity. Ann Pharmacother 2004;38:1419-23.

Nesto RW, Bell D, Bonow RO, et al. Thiazolidinedione use, fluid retention, and congestive heart failure: A consensus statement from the american heart association and american diabetes association. Oct. 7, 2003. Circulation 2003;108:2941-8.

Bruzzone S, Bodrato N, Usai C, et al. Abscisic acid is an endogenous stimulator of insulin release from human pancreatic islets with cyclic adp ribose as second messenger. J Bioi Chern 2008;283:32188-97.

Magnone M, Bruzzone S, Guida L, et al. Abscisic acid released by human monocytes activates monocytes and vascular smooth muscle cell responses involved in atherogenesis. J Bioi Chern 2009. 284: 17808-17818.

Watanabe M, Inukai K, Katagiri H, Awata T, Oka Y, Katayama S. Regulation of ppar gamma transcriptional activity in 3t3-11 adipocytes. Biochem Biophys Res Commun 2003;300:429-36.

Bassaganya-Riera J, Misyak S, Gun AJ, Hontecillas R. Ppar gamma is highly expressed in f4/80(hi) adipose tissue macrophages and dampens adipose-tissue inflammation. Cell Immunol 2009.

Bassaganya-Riera J, Reynolds K, Martino-Catt S, et al. Activation ofppar gamma and delta by conjugated linoleic acid mediates protection from experimental inflammatory bowel disease. Gastroenterology 2004;127:777-91.

Walczak R, Tontonoz P. Pparadigms and pparadoxes: Expanding roles for ppargamma in the control of lipid metabolism. J Lipid Res 2002;43:177-86. 55. Xu H, Barnes GT, Yang Q, et al. Chronic inflammation in fat plays a crucial role in the development of obesity-related insulin resistance, J Clin Invest 2003;112:1821-30.

Weisberg SP, McCann D, Desai M, Rosenbaum M, Leibel RL, Ferrante AW, Jr. Obesity is associated with macrophage accumulation in adipose tissue. J Clin Invest 2003; 112: 1796-808.

(56) References Cited

OTHER PUBLICATIONS

Kang K, Reilly SM, Karabacak V, et al. Adipocyte-derived thZ cytokines and myeloid ppardelta regulate macrophage polarization and insulin sensitivity. Cell Metab 2008;7:485-95.

Xu H, Barnes GT, Yang Q, et al. Chronic inflammation in fat plays a crucial role in the development of obesity-related insulin resistance. J Clin Invest 2003; 112:1821-30.

Odegaard JI, Ricardo-Gonzalez RR, Red Eagle A, et al. Alternative m2 activation ofkupffer cells by ppardelta ameliorates obesity-induced insulin resistance. Cell Metab 2008;7:496-507.

Hersoug LG, Linneberg A. The link between the epidemics of obesity and allergic diseases: Does obesity induce decreased immune tolerance? Allergy 2007;62: 1205-13.

Bassaganya-Riera J, Ferrera G, Casagrana 0, et al. F4/80hiccr2hi macrophage infiltration into the intra-abdominal fat worsens the severity of experimental ibd in obese mice with dss colitis e-SPEN, the European e-Journal of Clinical Nutrition and Metabolism 2009;4.

Suzuki A, Yasuno T, Kojo H, Hirosumi J, Mutoh S, Notsu Y. Aleration in expression profiles of a series of diabetes-related genes in db/db mice following treatment with thiazolidinediones. Jpn J Pharmacol 2000;84:113-23.

Bouhlel MA, Derudas B, Rigamonti E, et al. Ppargamma activation primes human monocytes into alternative m2 macrophages with anti-inflammatory properties. Cell Metab 2007;6: 137-43.

Odegaard JI, Ricardo-Gonzalez RR, Goforth MH, et al. Macrophage-specific ppargamma controls alternative activation and improves insulin resistance. Nature 2007;447:1116-20.

METHOD OF SYNERGISTICALLY ENHANCING THE THERAPEUTIC EFFICACY AND SAFETY OF MEDICATION THROUGH A COMBINATION THERAPY

STATEMENT OF RELATED APPLICATIONS

This application claims priority to U.S. Provisional Patent Application 61/147,773, filed Jan. 28, 2009 and U.S. Provisional Patent Application 61/234,864, filed Aug. 18, 2009. The disclosures of both of those applications are hereby incorporated herein.

FIELD OF THE INVENTION

The present invention relates to the field of medical treatments for diseases and disorders. More specifically, the present invention relates to the combined use of a therapeutically effective amount of abscisic acid and pharmaceuticals for a time sufficient to prevent and treat insulin resistance, cardiovascular disease, impaired glucose tolerance, diabetes and inflammation.

BACKGROUND OF THE INVENTION

Over the past two and a half decades there has been an epidemic growth in the rates of obesity in the United States. Approximately one-third of the country is now clinically obese and two-thirds are overweight (1), putting many at risk of increased risk of developing insulin resistance and contracting chronic diseases such as cardiovascular disease (CVD), type II diabetes (T2D), several types of cancer, stroke, gallbladder disease, and obstructive sleep apnea (2, 3).

One factor known to play an essential role in the development of obesity-induced insulin resistance is inflammation. Obesity is associated with higher systemic inflammation (4), and inhibiting essential inflammatory pathways has been shown to completely dissociate obesity from insulin resistance (5-8). Thus, it is not altogether surprising that many of the more effective anti-diabetic treatments are also anti inflammatory in nature. One such class of drugs is the thiazolidinediones (TZDs), which include rosiglitazone (AVANDIA) and pioglitazone (ACTOS). The TZDs insulin-sensitizing actions are mediated mainly through the nuclear receptor peroxisome proliferator-activated receptor $\gamma$ (PPAR $\gamma$) (9), which acts in a number of direct and indirect distinct mechanisms to reduce inflammation. As a key regulator of adipocyte differentiation, PPAR $\gamma$ agonists increase the number of adipocytes in the subcutaneous adipose tissue region (9), thereby preventing adipocytes in visceral adipose tissue from being hypertrophic and dysfunctional (10). The hypertrophy and inflammation of visceral adipocytes is thought to be one of the main initiating steps in the development of obesity induced chronic inflammation (11). Hypertrophic adipocytes, in addition to secreting fatty acids, which can wind up in unwanted places such as the liver, heart, blood vessels, and skeletal muscle, also become apoptotic and recruit pro-inflammatory macrophages into white adipose tissue (11, 12). PPAR $\gamma$ agonists inhibit monocyte migration and pro-inflammatory cytokine secretion from macrophages by blocking the activation of the pro-inflammatory transcription factor nuclear factor-$\kappa$B (NF-$\kappa$B) (13-15). The practical use for these compounds actually beyond diseases associated with obesity and insulin resistance as PPAR $\gamma$ activation has shown potential for treating various forms of cancer (i.e., lung, breast, colon) (16), multiple sclerosis (17), malaria (18), airway inflammation (19, 20), and autoimmune diseases (21-24), including intestinal inflammation, Crohn's disease, ulcerative colitis (25-27), arthritis (28), and dermatitis (29).

Despite their beneficial effects, TZDs are associated with a number of health risks, such as weight gain, fluid retention, and congestive heart failure that have limited their potential for use in many of the conditions described above (16). There are also side-effects associated with the biguanides, (i.e., metformin or Glucophage), which are also used currently to improve insulin sensitivity, such as lactic acidosis (30). It is in this context in which the present inventors began to investigate the ability of a natural compound, abscisic acid (ABA), to activate PPAR $\gamma$ without potentially dangerous side-effects. In their initial studies, they found that ABA increases PPAR $\gamma$ activity in vitro and, when supplemented into high-fat diets, significantly improves glucose tolerance and prevents adipose tissue inflammation in db/db mice (17). These effects were mitigated in mice deficient in PPAR $\gamma$ in immune cells (18). In all the studies performed, in which the longest period of ABA administration took place over 7 months, there were no side effects associated with the ABA-supplementation (17, 18).

Since the inventors' initial work, there have been studies showing that ABA increases pancreatic insulin secretion through a cyclic AMP (cAMP)/protein kinase A (PKA)-dependent mechanism (19), thus further elucidating ABA's mechanism of action in mammalian cells.

SUMMARY OF THE INVENTION

It is an object of the present invention to provide compositions for enhancing the efficiency of active compounds which contain the active compound in combination with abscisic acid (ABA). The active compounds which may be enhanced include anti-diabetic compounds, cardioprotective compounds and anti-inflammatory compounds. The compositions of the present invention show synergism between the active compounds and the ABA, allowing for increased efficacy of the active compound and the ABA. As such, the active compound and the ABA may be present at lower concentrations than when either of the agents are administered alone, allowing for reduction of side effects.

It is a further object of the present invention to provide methods for increasing the efficacy of active compounds by providing them in combination with ABA.

It is a further object of the present invention to provide methods for altering the expression or activity of PPAR $\gamma$ in a cell by contacting the cell with ABA and a thiazolidinedione in amounts sufficient to alter the expression or activity of PPAR $\gamma$ in a cell.

It is a further object of the present invention to provide methods for improving obesity related inflammation in at least one cell of a mammal by contacting the cell with ABA and a thiazolidinedione in amounts sufficient to alter the expression or activity of PPAR $\gamma$ in a cell.

It is a further object of the present invention to provide methods for decreasing apoptosis of pancreatic beta cells in mammalian subjects by administering to the subjects a composition containing an anti-diabetic agent and ABA.

It is yet a further object of the present invention to provide methods for increasing insulin secretion of pancreatic beta cells in mammalian subjects by administering to the subjects a composition containing an anti-diabetic agent and ABA.

BRIEF DESCRIPTION OF THE DRAWINGS

The accompanying drawings, which are incorporated in and constitute a part of this specification, illustrate several embodiments of the invention and together with the written description, serve to explain certain principles and details of embodiments of the invention.

DETAILED DESCRIPTION OF THE INVENTION

Figure 1:
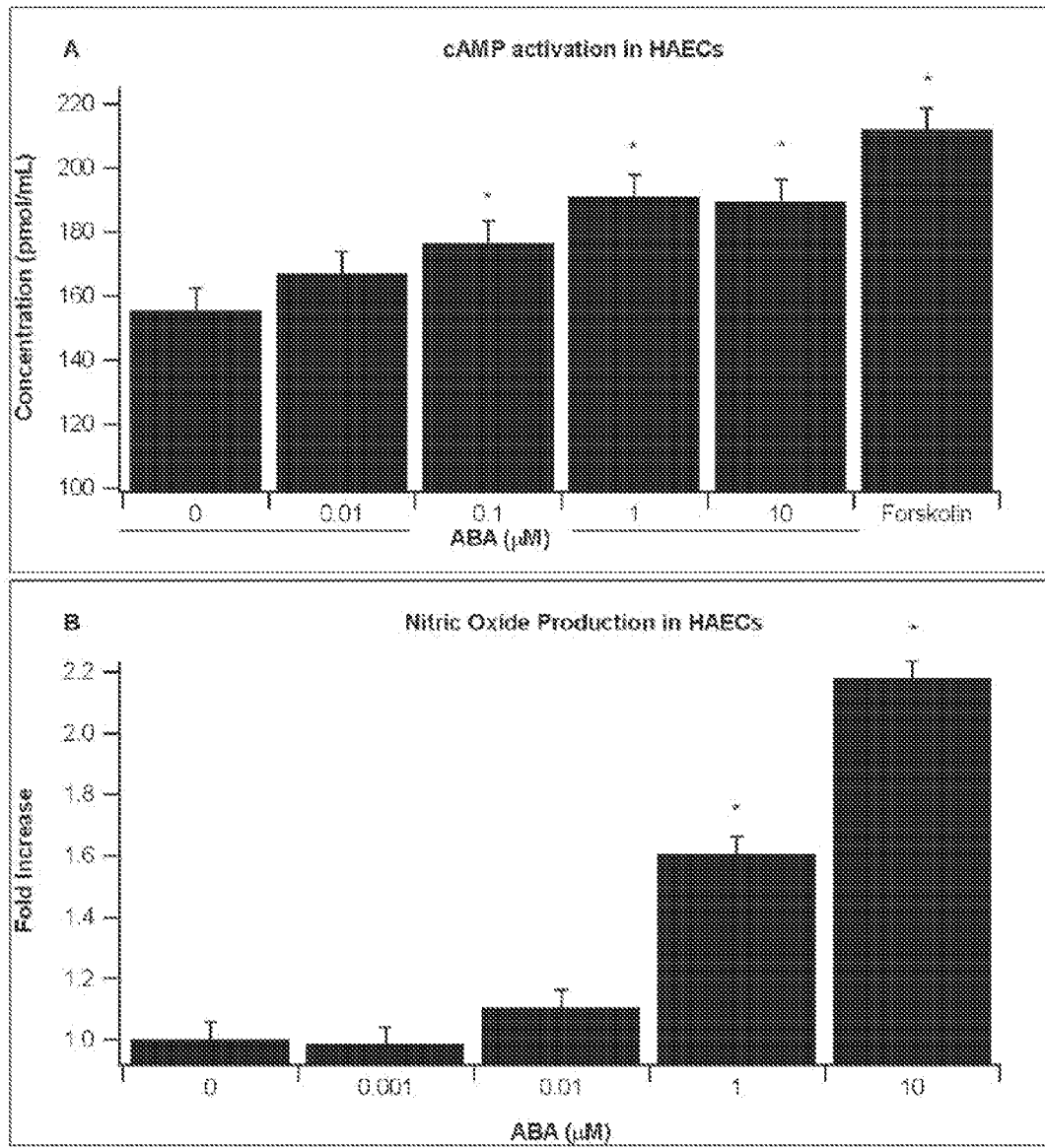
FIG. 1 shows the production of cyclic AMP (cAMP) by confluent human aortic endothelial cells (HAECs). These cells were serum-starved using HBSS buffer for 30 min and then stimulated with various concentrations of abscisic acid (ABA) or Forskolin (forsk, 1 uM) for 5 minutes. After removing supernatant, cells were lysed with 0.1 M HCL to measure nonacetylated cAMP. Results (pmol/ml) from four independent experiments are depicted. Data are represented as mean±standard error. Points with an asterisk are significantly different from the control.

The present invention provides new uses for abscisic acid and structurally related compounds. The term abscisic acid (ABA) herein refers to a plant hormone containing a trimethylcyclohexene ring with one or more hydroxy groups (for instance a 6-hydroxy group), a 3-oxo group and an unsaturated side chain in the sixth position of the trimethylcyclohexen ring containing cis-7, trans-9 double bonds, its non-toxic salts, active esters, active isomers, active metabolites and mixtures thereof. Non-toxic salts include, for example, alkyl esters having from 1 to 6 carbon atoms in the alkyl group, as well as mono-, di- and tri-glycerides, and mixtures thereof. Active isomers of abscisic acid include geometrical isomers and its non-toxic salts, e.g., sodium, potassium, calcium and magnesium salts, and its active esters, e.g., alkyl esters having from 1 to 6 carbon atoms in the alkyl group, as well as mono-, di- and tri-glycerides, and mixtures thereof. Active optical isomers of abscisic acid include the (+)-enantiomer and the (−)-enantiomer and its non-toxic salts, e.g., sodium, potassium, calcium and magnesium salts, and its active esters, e.g., alkyl esters having from 1 to 6 carbon atoms in the alkyl group, as well as mono-, di- and tri-glycerides, and mixtures thereof. Active metabolites of abscisic acid include oxygenated abscisic acid analogs, including but not limited to, 8'-hydroxyABA, (+)-7'-hydroxyABA, 2'3'-dihydroABA, 8'-hydroxy-2',3'-dihydroABA and its non-toxic salts, e.g., sodium, potassium, calcium and magnesium salts, and its active esters, e.g., alkyl esters having from 1 to 6 carbon atoms in the alkyl group, as well as mono-, di- and tri-glycerides, and mixtures thereof. Structurally related compounds, include but are not limited to, compounds containing conjugated double bonds (e.g., conjugated dienes, trienes and tetraenes) in the unsaturated side chain and compounds containing a trimethylcyclohexene ring with or without hydroxy moieties. For ease of reference, all such compounds are referred to herein generally at times as abscisic acid or ABA.

Based on new findings showing that ABA can activate an extracellular signaling cascade, the present invention discloses that ABA can work synergistically with natural and synthetic PPAR γ ligands. Abscisic acid is a natural compound that the inventors have found improves inflammation and glucose tolerance in part by acting through the nuclear receptor peroxisome proliferator activated receptor γ (PPAR γ). With reports that ABA can also act through the plasma membrane, it was realized that ABA can act as a synergistic activator of PPAR γ and other members of the PPAR family of nuclear receptors (PPARs α,δ) and, therefore, could enhance the efficacy and safety of a number of drugs which are currently available or will be available on the market. The studies presented herein showed a significant synergistic effect on PPAR γ activity when ABA was combined with rosiglitazone. The invention thus provides a drug combination therapy with synergistic effects in the treatment of diseases and disorders such as diabetes, obesity-related inflammation, cardiovascular disease, and other diseases and disorders involving PPARs. The combination can include other substances, including other bioactive substances, but preferably the combination, when administered to a subject, comprises abscisic acid and the second substance (e.g., a TZD) as the predominant bioactive agent directed to the disease or disorder of interest. As is expected by those of skill in the art, the combination can be supplied as two or more distinct things or as a combination of multiple substances (i.e., a composition). Uses for the combinations are discussed in detail below.

Abscisic acid may be a substantially pure single chemical compound or a mixture of one or more abscisic acid compounds as defined above. For example, the abscisic acid may be in the form of an extract obtainable or obtained from plant extracts, either directly or following one or more steps of purification or it can be chemically synthesized.

The abscisic acid used in the described methods may be in a free acid form or bound chemically through ester linkages. In its natural form, abscisic acid is heat stable. Abscisic acid may be used in its natural state or in a dried and powdered form. Further, the free acid form of abscisic acid may be converted into a non-toxic salt, such as sodium, potassium or calcium salts, by reacting chemically equivalent amounts of the free acid form with an alkali hydroxide at a basic pH. ABA and an exemplary compound falling within the definition of abscisic acid and structurally related compounds are disclosed, for example, in U.S. patent application publication number 2007/0184060A1, which is hereby incorporated by reference herein. Other structurally related compounds are known in the art, such as those disclosed by Hill et al. (45).

In certain embodiments, the invention provides for use of abscisic acid and structurally related compounds, such as a compound selected from the group consisting abscisic acid, esters thereof, pharmaceutically suitable salts thereof, metabolites thereof, structurally related compounds thereof, or combinations thereof, in combination with one or more (TZDs), such as rosiglitazone and pioglitazone, in the treatment and prevention of diseases and disorders associated with diabetes, cardiovascular disease, obesity, and inflammation. The present invention is directed to use of such compounds and combinations in the treatment and prevention of diseases and disorders associated with a molecular mechanism involving one or more PPARs, such as PPAR γ. For example, in certain embodiments, the invention relates to prevention and treatment of hyperglycemia, impaired glucose tolerance, insulin resistance, prediabetes, and type 2 diabetes, while in other embodiments, the invention relates to prevention and treatment of inflammation, including but not limited to obesity-related inflammation. The invention is based, at least in part, on the discovery that abscisic acid can affect the expression of PPAR γ, that the combination of ABA and (TZDs) provides surprising synergistic effects, and that the effects are relevant to all diseases and disorders that involve expression or activity of PPAR γ. While not being limited to any particular mode of action, it is possible that abscisic acid and its derivatives and structurally related compounds affect PPAR γ expression and/or activity, and that this activity is complementary to the activities of TZDs. However, the invention also contemplates other modes of action, such as by affecting expression or activity of any number of other cellular molecules, including, but not limited to, nuclear receptors that may be activated by ABA, including liver X receptor (LXR), retinoid X receptor (RXR), pregnane X receptor (PXR), vitamin D receptor (VDR), as well as nuclear receptor-independent mechanisms such as membrane initiated signaling through the activation of G protein-coupled receptors and stimulation of intracellular cyclic adenosine monophosphate production.

In other embodiments, the invention relates to use of ABA in combination with other pharmaceuticals, such as TZDs, for inhibition of infiltration of macrophages into skeletal muscle, white adipose tissue, blood vessel wall, and related inflammation. This inhibition can be found in vitro and in vivo. The effect results from exposing cells to ABA, preferably in combination with one or more other biologically active substances of the TZD family. In certain embodiments, the invention provides for treating subjects with ABA, preferably with another bioactive agent such as a TZD, for example as a dietary supplement, to reduce skeletal muscle macrophage infiltration, white adipose tissue macrophage infiltration, immune cell infiltration into the aortic wall, inflammation, or some or all of them. It also provides for treating a subject to achieve these goals, and additionally to treat a subject suffering from diabetes or heart disease, to treat a subject at risk for developing diabetes or heart disease, or to prevent a subject from developing diabetes or heart disease.

In certain aspects, the invention relates to methods of affecting the expression of PPAR γ in a cell. In general, the methods include contacting a cell with ABA and a TZD, preferably rosiglitazone or pioglitazone, in an amount or concentration sufficient to affect expression or activity of PPAR γ in the cell. These methods can be practiced either in vitro or in vivo. Where practiced in vitro, the methods can be used to study the expression of PPAR γ, to test other compounds for the ability to supplement or antagonize the effects of ABA, one or more TZDs, or both in combination, on PPAR γ expression, or for any other reason of importance to a researcher. When practiced in vivo, the methods can be used as a method of treating a subject for one or more diseases or disorders associated with PPAR γ expression. According to certain embodiments of the methods of the invention, preferably, expression of PPAR γ is increased. The step of contacting a cell can be any action that causes ABA and the other compound (e.g., a TZD) to physically contact one or more target cells. Thus, it can be by way of adding the bioactive agents directly to an in vitro culture of cells to be contacted, and allowing the agent(s) sufficient time to diffuse through the media and contact at least one cell. Likewise, it can be through addition of a dry composition comprising ABA and preferably a TZD to cells in an aqueous environment. Alternatively, it can be by way of administering ABA and preferably a TZD to a subject via any acceptable administration route, and allowing the body of the subject to distribute the compounds to the target cell through natural processes. Thus, the in vivo methods can be methods of localized or systemic delivery of ABA and another bioactive agent to a cell in animals, including all mammals and humans in particular.

In another aspect, the invention provides methods of treating a subject suffering from or at risk of suffering from a disease or disorder involving PPAR γ expression. In general, the methods include administering ABA or a composition comprising ABA, preferably in combination with another bioactive agent, such as a TZD, to a subject in need thereof, in an amount sufficient to affect the amount or activity of PPAR γ in at least one cell of the subject. In certain embodiments, the combination affects the expression of the PPAR γ gene, resulting in a change in PPAR γ mRNA levels in a cell. In other embodiments, the combination affects the amount of PPAR γ protein in a cell, preferably through increase in expression of the PPAR γ gene. In other embodiments, the combination affects the activity of the PPAR γ protein in a cell, preferably by increasing the amount of ABA and/or TZD in the cell. In preferred embodiments, PPAR γ mRNA expression, PPAR γ-responsive gene expression, such as CD36, AP2 (fatty acid binding protein 4) and adiponectin, protein levels, and/or protein activity is increased in a cell of the treated subject.

In the method of treating, administering the combination therapy can be through any known and acceptable route. Such routes include, but are not necessarily limited to, oral, via a mucosal membrane (e.g., nasally, via inhalation, rectally, intrauterally or intravaginally, sublingually), intravenously (e.g., intravenous bolus injection, intravenous infusion), intraperitoneally, and subcutaneously. Administering can likewise be by direct injection to a site (e.g., organ, tissue) containing a target cell (i.e., a cell to be treated). Furthermore, administering can follow any number of regimens. It thus can comprise a single dose or dosing of the bioactive agents, or multiple doses or dosings over a period of time. Accordingly, treatment can comprise repeating the administering step one or more times until a desired result is achieved. In certain embodiments of the present invention, treating can continue for extended periods of time, such as weeks, months, or years. Those of skill in the art are fully capable of easily developing suitable dosing regimens for individuals based on known parameters in the art.

The amount to be administered will vary depending on the subject, stage of disease or disorder, age of the subject, general health of the subject, and various other parameters known and routinely taken into consideration by those of skill in the medical arts. As a general matter, a sufficient amount of combination therapy will be administered in order to make a detectable change in the amount or activity of PPAR γ protein or mRNA or cyclic AMP concentrations in at least one cell of the subject to whom the combination is administered. Suitable amounts are disclosed herein, and additional suitable amounts can be identified by those of skill in the art without undue or excessive experimentation, based on the amounts disclosed herein.

The combination therapy will be administered in a form that is acceptable, tolerable, and effective for the subject. Numerous pharmaceutical forms and formulations for biologically active agents are known in the art, and any and all of these are contemplated by the present invention. Thus, for example, the combination therapy can be formulated in an oral solution, a caplet, a capsule, an injectable, an infusible, a suppository, a losenge, a tablet, a cream or salve, an inhalant, and the like.

In one aspect, the invention provides a method of treating or preventing a subject suffering from diabetes, or otherwise healthy individuals at risk for developing diabetes. According to the invention, the term "a subject suffering from diabetes" is used to mean a subject (e.g., animal, human) having a disease or disorder showing one or more clinical signs that are typical of diabetes. The term "a subject at risk for developing diabetes" is used to mean a subject in which one or more clinical signs of diabetes are not clearly shown, but who shows one or more sub-clinical signs that are typical of diabetes, or who has a family history that indicates a significant risk of developing diabetes. In general, the method of treating or preventing according to this aspect of the invention comprises administering to the subject an amount of combination therapy that is effective in treating or preventing one or more symptoms or clinical manifestations of diabetes, or in preventing development of such symptom(s) or manifestation(s).

Thus, according to the methods of the invention, the invention can provide methods of treatment of diabetes. The methods of treatment can be prophylactic methods. In certain embodiments, the methods are methods of treating type 2 diabetes (T2D), cardiovascular disease or inflammation. In certain other embodiments, the methods are methods of preventing diabetes, such as type 2 diabetes. In still other embodiments, the methods are methods of halting the progression of diabetes, such as type 2 diabetes. In still other embodiments, the methods are methods of improving the health status of a subject suffering from diabetes, such as type 2 diabetes. Accordingly, in certain embodiments, the invention provides methods of protecting the health, organs, and/or tissues of a subject suffering from diabetes or at risk for developing diabetes.

In one exemplary embodiment of the invention, the methods of treating diabetes comprises treating diabetes without causing significant weight gain in the subject being treated. That is, it has been found that the methods of treating according to the present invention provide a treatment effect without causing a significant gain in weight, for example by fluid retention, in the subject being treated, as compared to other similar subjects not receiving the treatment. While not wishing to be bound by any particular theory as to why this effect is seen, it is likely that treatment with combination therapy, while causing an increase in PPAR γ expression in some cells, does not cause over-expression or over-activation, as is commonly seen with some other (e.g., synthetic) PPAR γ agonists currently known for treatment of diseases associated with PPAR γ. In addition, the use of combination therapy according to the present invention maintains or enhances the effectiveness of ABA alone or TZDs alone, but reduces or eliminates adverse side effects seen with TZDs alone. The present methods have proven effective in diabetes and hypertension treatments, and allow for reduction in amounts of either bioactive compound used in treatments, thus lowering the likelihood of side-effects.

In view of the above-mentioned molecular basis for at least part of the effect seen, the present invention provides methods of treating diabetes by increasing the expression of PPAR γ in at least one cell of the subject being treated. As with other methods of the invention, these methods include administering a combination of bioactive agents to a subject suffering from diabetes, where the combination is administered in an amount sufficient to increase the expression, activity, or amount of PPAR γ in at least one cell of the subject. In certain embodiments, the diabetes is type 2 diabetes. In these methods, the cell(s) in which PPAR γ expression, level, or activity is increased can be any cell, from any tissue or organ, in the subject treated. In preferred embodiments, the cell(s) are white adipocyte tissue (WAT) cells, pancreatic cells, or both. In certain treatment methods, the methods do not cause an equivalent increase in PPAR γ expression, level, or activity in liver cells, as compared to the increase seen in WAT and/or pancreatic cells. In certain embodiments, no detectable increase in PPAR γ mRNA or protein is seen in a liver cell of a subject being treated. One exemplary embodiment of this aspect of the invention is a method of treating diabetes in which expression of PPAR γ is increased in certain cells of the subject, but not other cells, and in which the level of expression is not so high as to cause serious (or, in embodiments, any) noticeable or detectable deleterious effects on the short-term or longterm health of the subject. For instance, uncontrolled overactivation of PPAR γ in the liver could lead to liver injury. In treating diabetes according to the methods of the present invention, one effect that may be seen is an increase in interscapular brown adipose tissue (BAT) mass, which is a positive effect in the context of treatment of diabetes.

In yet another aspect of the invention, methods of lowering glucose levels are provided. These methods include administering a combination therapy to a subject suffering from diabetes or at risk of suffering from diabetes. The combination therapy is administered in an amount sufficient to lower the glucose levels in the patient, and especially to lower levels of free glucose in the blood of the subject. Lowering can occur at any time under any physiological condition, but is preferentially seen with regard to the subject's fasting glucose level. In related methods of the invention, methods of increasing the glucose tolerance of a subject are provided. The methods include the same steps as other methods of the invention, and are similarly based, at least in part, on the underlying mechanisms of action of the combination therapy, and the surprisingly selective nature of the effects of the combination therapy on certain cells, but not others. In addition, like the other methods, these methods are based, at least in part, on the low toxicity of the combination therapy and, as a corollary, the high activity of the combination therapy in affecting PPAR γ expression and cyclic AMP production.

As such, the methods can provide methods of reducing inflammation, including obesity-related inflammation. The methods can reduce inflammation systemically (i.e., throughout the subject's body) or locally (e.g., at the site of administration or the site of inflammatory cells, including but not limited to T cells and macrophages). In treating or preventing obesity-related inflammation according to the methods of the present invention, one effect that may be seen is the decrease in the number of macrophages infiltrating the white adipose tissue, skeletal muscle tissue, blood vessels and a downregulation of tumor necrosis factor-alpha expression in adipose tissue, skeletal muscle tissue and blood vessels. The methods can thus also be considered methods of affecting or altering the immune response of a subject to whom the ABA combination therapy is administered.

In view of the above methods, it should be evident that the present invention provides ABA combination therapy for use in contacting cells, such as in treating cells of a subject. The above discussion focuses on the use of ABA and another bioactive compound, such as a TZD, as part of a composition for use in what could generally be considered a pharmaceutical, nutritional supplement, dietary aid, or food additive.

In other embodiments, the present invention provides compositions for administration to mammals. The compositions contain ABA and another bioactive compound, such as antidiabetic compounds, cardioprotective compounds, and anti-inflammatory compounds. Non-limiting examples of active compounds which may be used in the compositions of the present invention are also listed in the Examples below.

Examples of anti-diabetic compounds that may be used in compositions of the present invention include PPAR γ agonists, glitazars, conjugated linoleic acids, dual PPAR α/γ agonists, glucagon-like peptide receptor 1 agonists and biguanides. PPAR γ agonists may include TZDs such as rosiglitazone and pioglitazone. Biguanides may include metformin and glucophage.

Examples of cardioprotective compounds include PPAR α agonists, guanylate cyclase activators, angiotensin converting enzyme inhibitors, angiotensin II type 1 blocker or lipid-lowering drugs. The PPAR α agonist may be a fibrate drug such as clofibrate, gemfibrozil and fenofibrate. The lipid lowering drug may be a statin such as atorvastatin, cerivastatin, fluvastatin, lovastatin, mevastatin, pitavastatin, pravastatin, rosuvastatin and simvastatin, in their free acid or pharmaceutically acceptable salt forms.

The compositions of the present invention may include a carrier suitable for administration to a mammal. As is described above, the compositions may be in the form of oral solution, a caplet, a capsule, an injectable, an infusible, a suppository, a lozenge, a tablet, a cream or salve, an inhalant, and the like. In certain embodiments, the compositions are pharmaceutical compositions containing a pharmaceutically acceptable carrier which may be a sugar, a starch, a binder, a disintegrant, a lubricant, a polymer, a dye, a flavoring, a buffer, a salt solution and other excipients for solid and liquid pharmaceutical forms are as well known in the art.

In other embodiments, the carrier may be a food, a drink, a nutritional supplement, such as a vitamin or a dietary aid. The compositions of the present invention may be formed by adding ABA and another active compound to a known food or drink to form a functional food or drink. The compositions may also be formulated as vitamins or dietary aids in solid or liquid form including excipients such as those described above and other known excipients for formulating nutritional supplements.

The compositions of the present invention may contain the other active agent and/or ABA in concentrations that are lower than those usually required for administration of either agent alone. Even though these combinations may have lower concentrations of either the other active agent or ABA, the efficacy of either agent may be the same or better than higher concentrations of either agent alone. Without wishing to be bound by theory, the combination of the other active agent with ABA appears to synergistically enhance both the function of the other active agent and the ABA.

The concentrations of the other active agent in the compositions of the present invention may vary widely as is needed. In certain embodiments, the compositions may be administered at ABA concentrations of about 1 µg/kg to about 1 g/kg, as is required. In certain embodiments, the compositions are administered at ABA concentrations of about 1 mg/kg or more, about 10 mg/kg or more or about 100 mg/kg or more.

The concentrations of the other active agent will vary based on the other active agent used. One of skill in the art will be able to determine the concentration of the other active agent based on established concentrations known in the art. In certain embodiments, the concentrations of the other active agent will be about 100% of the concentration of the agent when administered alone, about 90% or more of the concentration of the agent when administered alone, about 75% or more of the concentration of the agent when administered alone, about 50% or more of the concentration of the agent when administered alone or about 25% or more of the concentration of the agent when administered alone.

As should be evident, the ABA combination therapy may be provided in a pharmaceutically acceptable form. Thus, ABA combination therapy can be provided in a form that is suitable for administration to a subject in need of it. It also may be present as a component of a composition, and in particular, a pharmaceutical composition. The ABA combination therapy may be provided as mixture of purified or semi-purified substances, or as a part of a simple or complex composition. Where present as part of a composition, the composition as a whole should be biologically tolerable at the amount to be exposed to a living cell. Thus, the composition may comprise toxic or otherwise deleterious substances when in its as-produced state, but be rendered non-toxic at a later date by further treatment or simply by dilution. The pharmaceutical composition may comprise any number of substances in addition to ABA and a second bioactive agent, preferably a TZD, such as, but not limited to, water, salts, sugars, buffers, biologically active compounds having no significant effect on PPAR γ, and drugs having no significant effect on PPAR γ.

EXAMPLES

The invention will be further explained by the following examples, which are intended to be purely exemplary of the invention, and should not be considered as limiting the invention in any way. In the Examples and throughout this specification, all percentages, part and ratios are by weight unless indicated otherwise.

Example 1

Synergistic Effect of ABA and Rosiglitazone

Research Design and Methods
A. Intracellular cAMP Assessment and Nitric Oxide Assessment Confluent human aorta endothelial cells (HAECs) were serum-starved using HBSS buffer for 30 min, then stimulated with various concentration of ABA and Forskolin (1 uM) for 5 min, after removing supernatant, cells were lysed with 0.1 M HCL to measure non-acetylated cAMP using a commercially available kit (Cayman chemical) following the manufacturer's instructions. Results (pmol/mL) were obtained from four independent experiments. For nitric oxide (NO), confluent HAECs were serum-starved for 30 min by using HBSS buffer, then treated with ABA for 15 min. Supernatant was used to measure NO using an fluorescent kit.

B. Transfection with ABA and Rosiglitazone

A pCMX.PPAR γ expression plasmid and a pTK.PPRE3x luciferase reporter plasmid driven by the PPRE-containing Acyl-CoA oxidase promoter were purified using Qiagen's Maxi kit (Valencia, Calif.). RAW 264.7 (American Type Culture Collection, Manassas, Va.) were grown in 24-well plates in DMEM high glucose medium (Invitrogen, Carlsbad, Calif.) containing 10% fetal bovine serum (FBS). The cells cultured in 24-well plates were co-transfected with 0.6 µg plasmid DNA and 1 ng of pRL reporter control plasmid per well using F-2 transfection reagents (Targeting Systems, Santee, Calif.) according to the manufacturer's protocol. Transfection efficiencies were determined by cotransfecting the cells with a pcDNA™ 3.1/His/lacZ control vector at 24 h. The transfected cells were then treated with rosiglitazone (0, 1, 10 µM; Cayman Chemicals, Ann Arbor, Mich.) with or a racemic ABA mixture (10 µM; Sigma). Transfected cells were harvested in reporter lysis reagent. Luciferase activity, normalized to pRL activity in the cell extracts was determined by using the dual luciferase reporter assay system (Promega, Madison, Wis.) in a TD-20/20 Single-Tube Luminometer (Turner Biosystems, Sunnyvale, Calif.). Relative luciferase activity (RLA) was calculated as a ratio of the chemiluminescence 10 seconds after the Luciferase Assay Reagent II (Promega) was added over the chemiluminescence 10 seconds after the Stop&Glo Reagent (Promega).

C. Statistical Analyses
Data were analyzed as a completely randomized design. To determine the statistical significance of the model, analysis of variance (ANOVA) was performed using the general linear model procedure of Statistical Analysis Software (SAS) as previously described (31). A $P<0.05$ was considered to be significant. When the model was significant, ANOVA was followed by Fisher's protected LSD multiple comparison method.

ABA increases intracellular levels of cAMP and nitric oxide in a dose-dependent manner To assess the ability of ABA to increase intracellular levels of these secondary messengers, the ability of ABA to increase cAMP and nitric oxide in human aortic endothelial cells (HAECs) was assessed. It is well-established that cAMP activation increases nitric oxide production (31). It was found that ABA, beginning at 0.1 uM, significantly increased intracellular cAMP concentration and nitric oxide production (see FIG. 1).

Results and Discussion

ABA Synergistically Enhances TZD Activity

Figure 2:
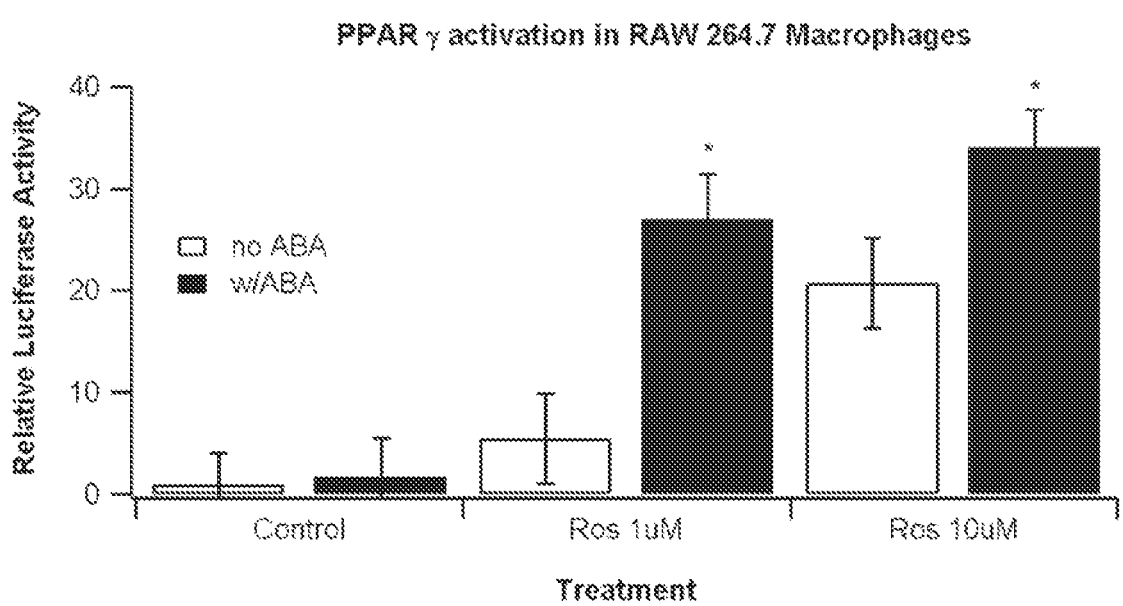
FIG. 2 shows synergistic activation of PPAR γ reporter activity by ABA in combination with rosiglitazone in RAW 264.7 macrophages. Cells were transiently transfected with a PPAR γ overexpression vector and PPRE luciferase construct. After 20 hours, cells were treated with rosiglitazone (0, 1, 10 uM) with or without abscisic acid (10 uM). Relative luciferase activity as assessed 20 hours after treatments. Data are presented as mean±standard error. An asterisk over a bar signifies that the "with ABA" treatment is significantly greater than the "no ABA" treatment at the same concentration of rosiglitazone.

It was hypothesized that ABA may increase PPAR γ activity by enhancing the activation of natural or synthetic ligands. To test this, RAW 264.7 macrophages were transfected with rosiglitazone (1, 10 µM) with and without ABA (10 µM). The results show a significant interactive effect (P=0.0345) between ABA and rosiglitazone, indicative of a synergistic enhancement by ABA (FIG. 2). It was discovered that ABA is a synergistic activator of PPAR γ.

Example 2

Synergistic Efficacy of ABA/PPAR Agonists Combination Therapies

In 2000, Lazennec et al. showed that cAMP/PKA activation augments PPAR activity in both the presence and absence of PPAR ligands by enhancing DNA binding (20). With these findings, there is strong potential for ABA to be used in conjunction with a TZD, such as rosiglitazone (AVANDIA), pioglitazone (ACTOS), ciglitazone, to treat any of the diseases which can be enhanced or improved by increased PPAR γ activity. These include diseases associated with insulin resistance (i.e., cardiovascular disease, type II diabetes, atherosclerosis, stroke, gallbladder disease, hypertension), cancer, autoimmune disorders, or any other condition in which decreasing the inflammatory response is the physician-recommended course of action. It was discovered that by combining a TZD with ABA, one will need to apply a significantly smaller dose of the drug to induce its effects. As stated in U.S. Pat. No. 6,515,132, the current minimum effective drug dose (µmol/kg diet) for TZDs are as follows: Rosiglitazone 3; Pioglitazone 200; Englitazone 200; Troglitazone 600; Ciglitazone 3000. These doses are known to result in off target side effects. However, if administered in combination with ABA, the effective doses of all these drugs are lower and the side effects diminished. Surprisingly, the combination does not provide additive effects, but instead shows synergistic effects.

ABA also acts synergistically with activators of PPAR α, PPAR δ, and dual- or pan-PPAR activators (20). PPAR α activators fall under the fibric acid class of hyperlipidemia drugs, which among them include fenofibrate (brand names: ANTARA, FENOGLIDE, LIPOFEN, LOFIBRA, TRICOR, TRIGLIDE, LIPIDIL MICRO, DOM-FENOFIBRATE, LIPIDIL SUPRA, LIPIDIL EZ), gemfibrozil (LOPID), and clofibrate (ATROMID-S). The PPAR δ agonist, CER-002 by Cerenis Therapeutics, successfully completed Phase I of clinical trials in May, 2008, but it is not yet commercially available. Dual-PPAR agonists, such as muraglitazar (PARGLUVA) and tesaglitazar (GALIDA), which has been discontinued by the company AstraZeneca as of this writing), are relatively new on the market, and combined use with ABA would significantly enhance their effectiveness.

Example 3

Synergistic Efficacy of ABA and Other Anti-Diabetic Medications

Figure 4:
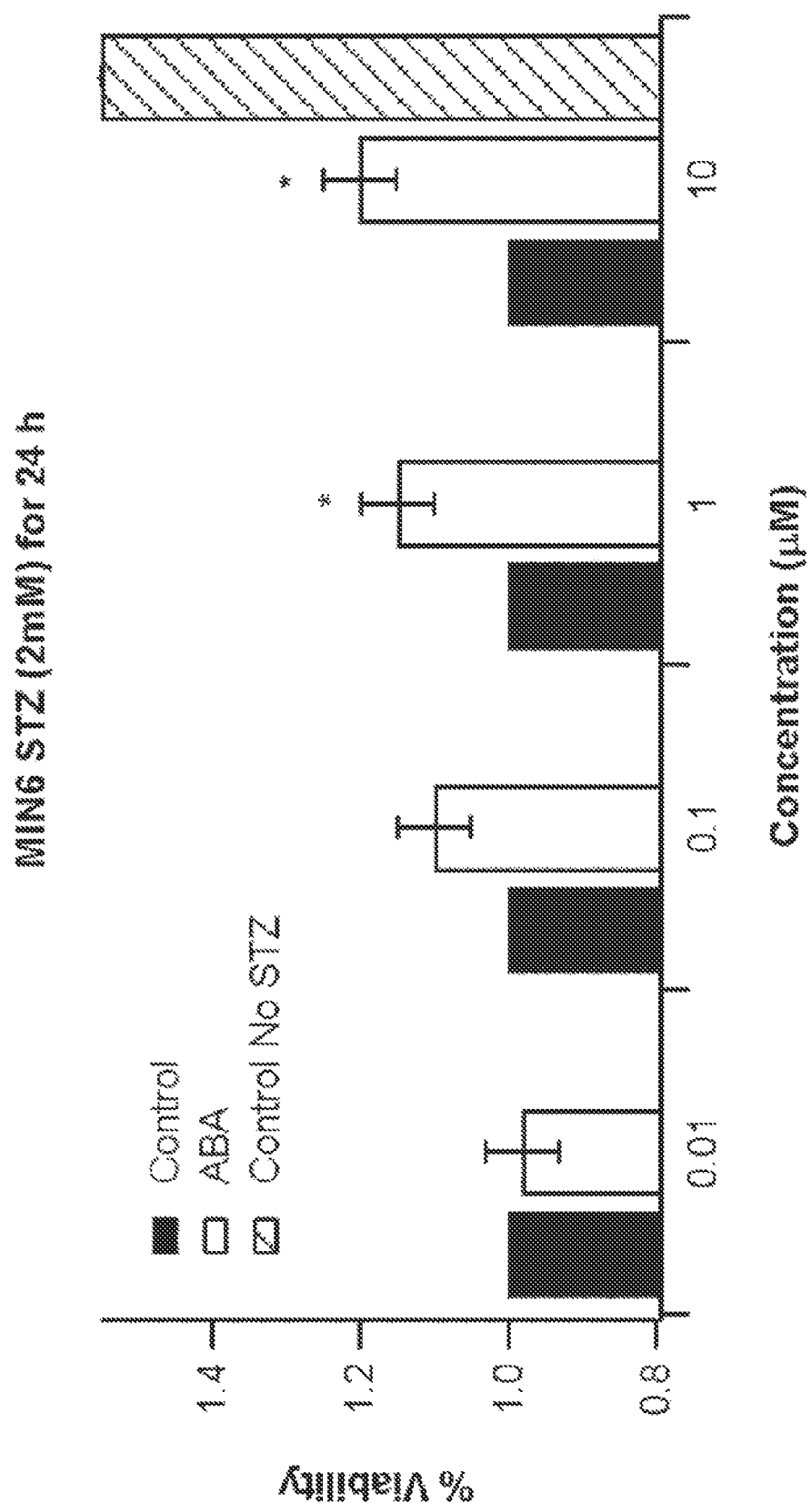
FIG. 4 shows that ABA at 1 and 10 micromolar concentrations increases the viability of insulin-secreting pancreatic beta cells following a challenge with streptozotocin (STZ) at 2 mM for 24 hours. Data are presented as mean±standard error.
Figure 5:
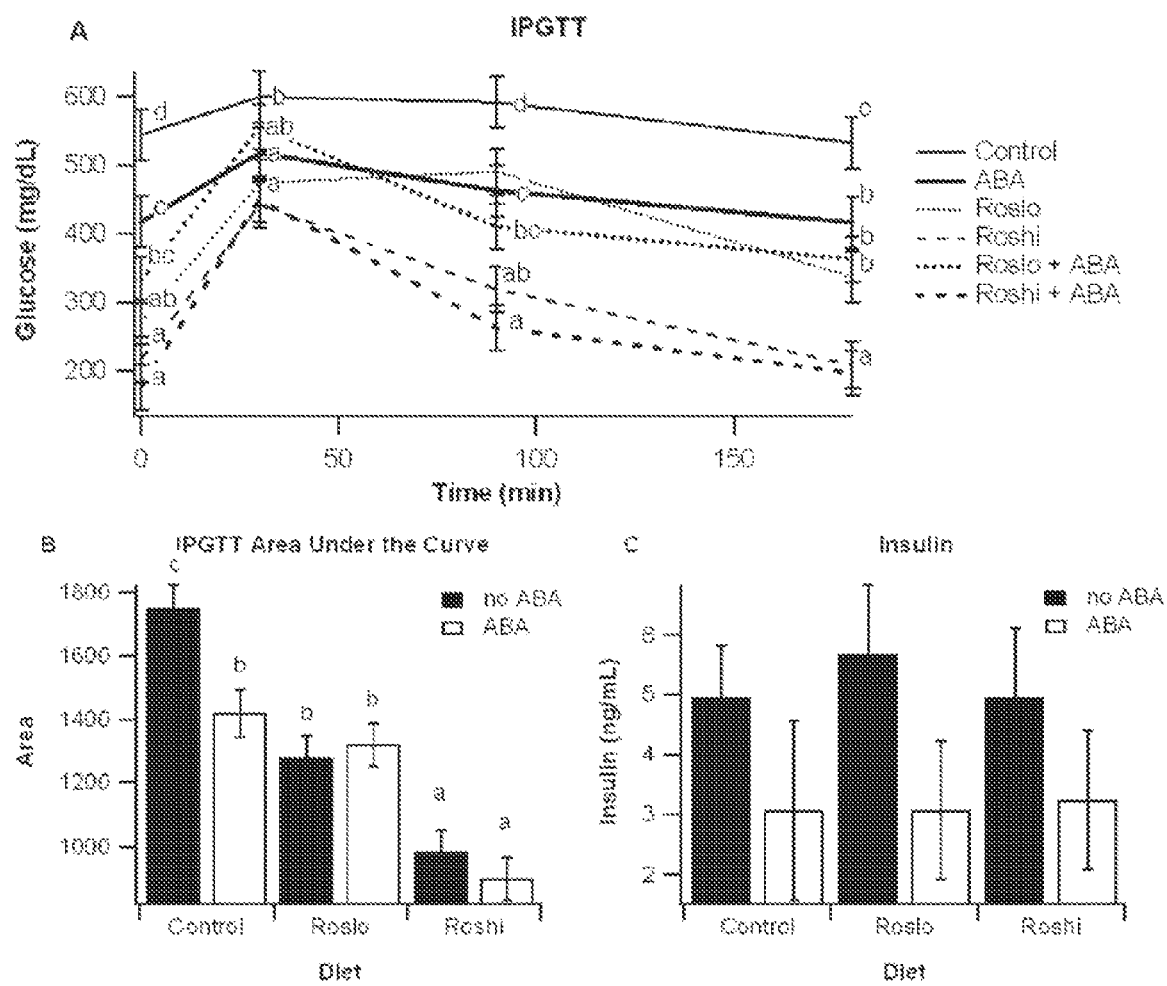
FIG. 5 shows the effect of abscisic acid (ABA) and rosiglitazone (Ros) on glucose tolerance and fasting insulin. Obese db/db mice were fed high-fat diets containing 0.15, or 70 mg/kg diet rosiglitazone maleate (control, $Ros^{lo}$, and $Ros^{hi}$, respectively) with and without racemic ABA (100 mg/kg diet). On day 42 mice underwent an intraperitoneal glucose tolerance test (IPGTT) (A). Areas under the curve (B) were calculated for each treatment. On day 55 fasting insulin levels were measured for mice on each diet (C). Data are represented as mean±standard error. Points with different subscripts are significantly different from each other (P<0.05).

In addition to activating PPARs, ABA also can act in concert with different types of oral anti-diabetic agents to increase effectiveness. These include the biguanides, which are already used in conjunction with TZDs (i.e., AVANDAMET, ACTOPLUS MET), the mineral chromium picolinate, and the sulfonylureas, which have repeatedly shown PPAR γ-agonistic activity (32,33). Members of the sulfonylurea class of insulin secretors include glipizide (GLUCOTROL), gliclazide (DIAMICRON), glibenclamide (DIABETA, GLYNASE, MICRONASE for U.S., DAONIL, SEMI-DAONIL, EUGLUCON for U.K.), gliquidone (GLURENORM), glyclopyramide (DEAMELIN-S), and the third-generation drug glimepiride (AMARYL). ABA can also increase the efficacy of glucagon-like peptide 1 receptor agonists, such as Liraglutide and Exenatide, and dipeptidyl peptidase IV (DPPIV) inhibitors, which prevent the metabolism of GLP-1 (32). GLP-1 and its receptor agonists increase insulin secretion from pancreatic beta cells through a cAMP-dependent mechanism (32,33). Because the mechanism of ABA action is still unknown, it is possible that ABA is acting to potentiate a cAMP response induced by other compounds like GLP-1 rather than having a direct response on its own. In addition, ABA diminishes pancreatic beta cell apoptosis caused by streptozotocin (FIG. 4), representing yet another mechanism by which ABA increases the efficacy of anti-diabetic medications.

In previous research, it was found that ABA can act unilaterally to reduce adipose tissue inflammation and improve glucose tolerance in obese mice (17, 18). The present invention teaches that ABA synergizes, rather than just adds to, anti-diabetic drug activity, and there exists the significant potential to combine ABA with PPAR agonists or other drugs for treating disease and disorders. By using the present ABA combination therapy one would enhance the positive effects of anti-diabetic drugs while limiting dosage.

Example 4

Synergism of ABA with Cardioprotective, Lipid-Lowering and Vasodilatory Drugs ABA lowers systolic blood pressure in ApoE-deficient mice and increases nitric oxide production from human aorta endothelial cells (see FIG. 1). Based on this finding, it was recognized that ABA also should significantly enhance the efficacy of cardioprotective drugs, thereby enhancing the range of the effects and potentially limiting the dosage needed for a desired effect. Among these drugs include the anti-hypertensive angiotension II inhibitors, such as eprosartan (TEVETEN), olmesartan (BENICAR), telmisartan (MICARDIS), valsartan (DIOVAN), irbesartan (AVAPRO), losartan (COZAAR), and candesartan (ATACAND), and angiotensin II converting enzyme inhibitors, including perindopril (ACEON), quinapril (ACCUPRIL), trandolapril (MAVIK), fosinopril (MONOPRIL), enalapril (VASOTEC), lisinopril (ZESTRIL), and captopril (CAPOTEN), and any drug in which one of these compounds is featured. Products such as ABA, which can activate cAMP, inhibit the synthesis of angiotensinogen, a precursor to the vasoconstrictor angiotensin II. Therefore, it is recognized that ABA can significantly boost the effectiveness of this type of drug (34).

There are a number of other drugs in the cardioprotective family that also have significant potential for being boosted by cotreatment with ABA. These include β-andrenergic receptor blockers, drugs that activate guanylate cyclase, drugs in the statin family, and drugs that activate PPAR α (previously mentioned). The first of those mentioned, the β andrenergic receptor blockers, function by inhibiting the actions of endogenous catecholamines, such as epinephrine and norepinephrine, which act through a cAMP-dependent mechanism. Based on this data, the ABA-induced increase in cAMP may interfere with catecholamine induction of cAMP as well, providing an enhanced benefit of these drugs or limiting their dosage. Among these drugs are cardioselective beta blockers, including metoprolol (TOPROL-XL, LOPRESSOR), nebivolol (BYSTOLIC), atenolol (TENORMIN), esmolol (BREVIBLOC), betaxolol (KERLONE), acebutolol (SECTRAL), and bisoprolol (ZEBETA), and non-cardioselective beta blockers, including propranolol (INNOPRAN XL, INDERAL, INDERAL LA), nadolol (CORGARD), carvedilol (COREG, COREG CR), sotalol (BETAPACE, BETAPACE AF), and timolol (BLOCADREN). In addition, it was recognized that ABA can enhance the activity of drugs that activate guanylate cyclase.

Cyclic AMP is formed in under the influence of nitric oxide (35, 36), which it has been shown to be produced following ABA treatment endothelial cells. Based on these findings, it was recognize that ABA is able to synergize with drugs belonging to the statin family, which lower cholesterol synthesis by inhibiting the enzyme HMGCoA reductase. Drugs in this category include lovastatin, simvastatin, atorvastatin, fluvastatin, pravastatin, and rosuvastatin. The link between ABA and statins may be linked to close interrelation between statins and nuclear receptors, particularly PPAR γ. Studies have shown added cardiovascular benefits when the use of statins was combined with TZDs (37), and statins have also been shown to enhance the activity of nuclear receptors such as PPAR α and to increase prostaglandin production to act on PPAR γ (38, 39).

Example 5

Synergistic Efficacy of ABA with Agonists of Retinoid X Receptor (RXR) and Retinoic Acid Receptor (RAR)

Research Design and Methods

A. Transfection of ABA with 9-Cis Retinoic Acid or Retinoic Acid

A pCMX.L-RXR or pCMX.RAR expression plasmid and a luciferase reporter plasmid were purified using Qiagen's Maxi kit (Valencia, Calif.). 3T3-L1 preadipocytes (American Type Culture Collection, Manassas, Va.) were grown in DMEM high glucose medium (Invitrogen, Carlsbad, Calif.) containing 10% fetal bovine serum (FBS). The cells cultured in 25 cm$^2$ flasks were co-transfected with 0.6 ug plasmid DNA and 1 ng of pRL reporter control plasmid per well using F-2 transfection reagents (Targeting Systems, Santee, Calif.) according to the manufacturer's protocol. After 24 hours, transfected cells were split trypsin and seeded into 96-well white plates at a concentration of 20,000 cells/wells. The transfected cells were then treated with 9-cis retinoic acid (0, 10 μM; Sigma), or retinoic acid (RA, 10 μM; Sigma), with ABA (10 μM; Sigma) Transfected cells were harvested in reporter lysis reagent. Luciferase activity, normalized to pRL activity in the cell extracts was determined by using the dual luciferase reporter assay system (Promega, Madison, Wis.) in a Modulus 96-well plate reader (Turner Biosystems, Sunnyvale, Calif.). Relative luciferase activity (RLA) was calculated as a ratio of the chemiluminescence 10 seconds after the Luciferase Assay Reagent II (Promega) was added over the chemiluminescence 10 seconds after the Stop&Glo Reagent (Promega).

B. Statistical Analyses

Data were analyzed as a completely randomized design. To determine the statistical significance of the model, analysis of variance (ANOVA) was performed using the general linear model procedure of Statistical Analysis Software (SAS) as previously described (31). A P<0.05 was considered to be significant. When the model was significant, ANOVA was followed by Fisher's protected LSD multiple comparison method.

Results and Discussion

Figure 3:
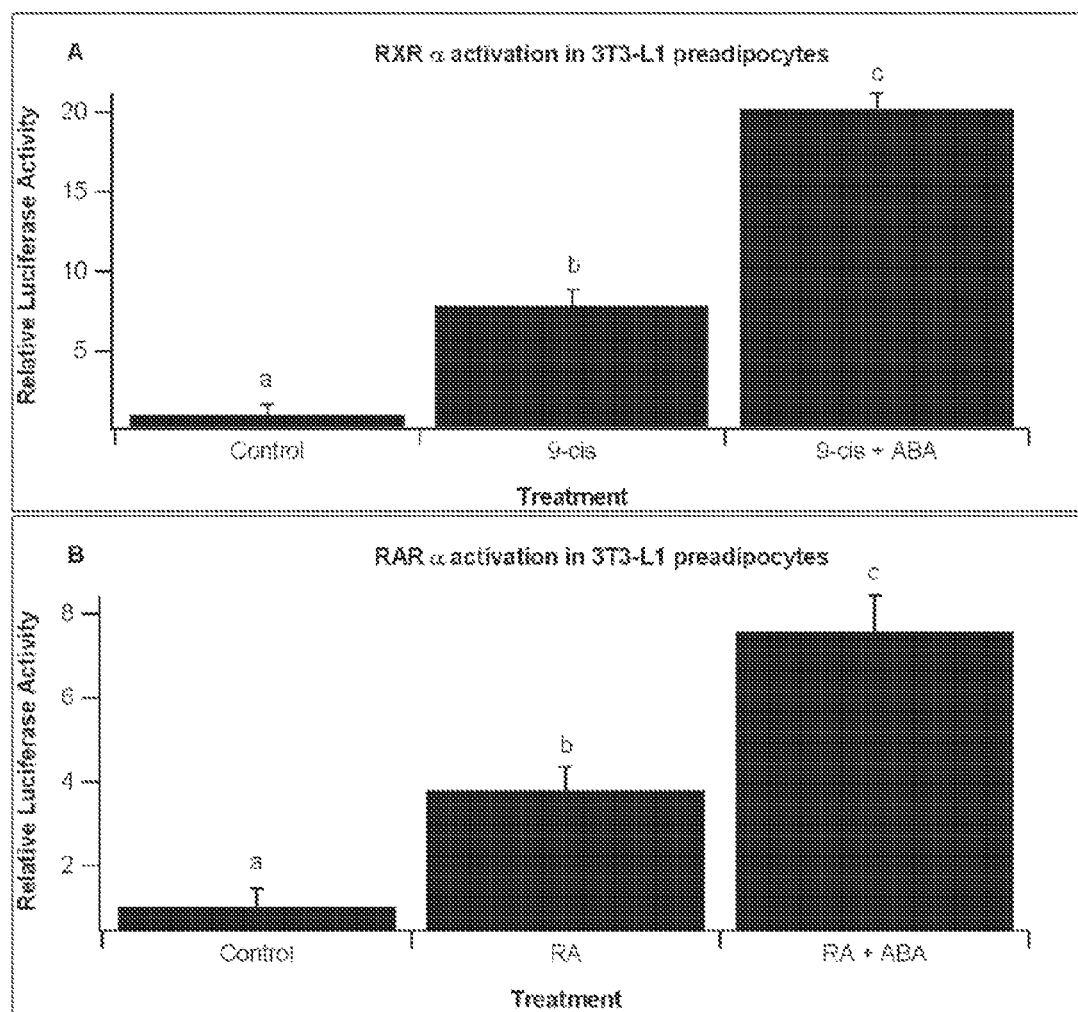
FIG. 3 shows synergistic activation of retinoid X receptor (RXR) and retinoic acid receptor (RAR) activity by abscisic acid. Data are presented as mean±standard error.

The results show that ABA synergistically enhances the activity of RXR and RAR ligands at 10 µM (FIG. 3). These results suggest that ABA can be used in combination with drugs or nutritional compounds (e.g., vitamin A) that target one or both of these receptors to limit drug dosage and toxicity. RXR α forms heterodimers with a number of other nuclear receptors, including the PPARs, the vitamin D receptor, and RAR, and has been the focus of anticarcinogenic and anti-diabetic research (40-42), and it has been suggested that combination of RXR agonists with cAMP activators may provide enhanced benefit for treating certain types of cancers (41). Because it is fat soluble, vitamin A can cause toxicity when taken in high doses. ABA can enhance the effect of the maximum allowable dosage of retinoic acid without causing toxicity.

Example 7

Abscisic Acid Synergizes with Rosiglitazone to Down-Modulate Macrophage Accumulation and Inflammation in Abdominal Adipose Tissue Introduction Over the past two decades the onset of obesity in the United States and worldwide has risen to epidemic proportions. According to recent estimates of 33% of the U.S. population is overweight and over 60% is obese [1]. This high prevalence of obesity has led to an increase in obesity-related diseases, including type II diabetes, cardiovascular disease, and stroke, and, according to a recent meta-analysis, is responsible for 9.1% of all health care-related expenditures in the United States [43]. Thus, novel approaches for preventing obesity-related illnesses are both timely and urgently required.

It is in this regard that the isoprenoid phytohormone abscisic acid (ABA) shows promise as a putative therapeutic against obesity-related inflammatory complications. ABA is a vitamin A derivative that is effective in improving glucose homeostasis and reducing obesity-related inflammation in obese and overweight mice [44]. Based on its ubiquitous presence in plants and the recent finding that it can be synthesized by mammalian cells [45], it may be well-tolerated by the human body. The studies have shown that ABA increases the activity of the nuclear receptor peroxisome proliferator-activated receptor γ (PPAR γ) in 3T3-L1 preadipocytes and that its full anti-diabetic effects are dependent on the presence of PPAR γ in immune cells [44,46]. PPAR γ is the molecular target of the thiazolidinedione (TZD) class of anti-diabetic drugs, which includes rosiglitazone maleate (AVANDIA), pioglitazone (ACTOS) and troglitazone which was removed from the market due to its hepatotoxicity [9,47]. Whereas TZD usage has been shown to be associated with significant side effects such as excessive fluid retention, liver damage and weight gain [48], there were no detectable side-effects in mice fed ABA at doses ranging from 100 to 800 mg/kg of diet [44].

Recent studies have shown that ABA also acts as an activator of the cAMP/PKA second messenger system in pancreatic and immune cells [49, 50]. Interestingly, PKA can activate PPAR γ indirectly through a phosphorylation-dependent mechanism [51]. In light of these findings, the objective of this study was to more closely examine the similarities between ABA and rosiglitazone (AVANDIA) as treatments for obesity-related inflammation and diabetes, and to investigate a potential synergistic interaction between the two compounds in modulating glucose tolerance and inflammatory macrophage accumulation in WAT. In this study obese/diabetic db/db mice were fed high-fat diets containing 0, IS, or 70 mg/kg rosiglitazone maleate (control, $Ros^{lo}$, and $Ros^{hi}$ respectively), each with or without racemic ABA (100 mg/kg). The results show that ABA acts similar to $Ros^{lo}$ in improving glucose tolerance in obese mice but also lowers insulin levels and, unlike Ros, it does not induce weight gain or fluid retention. Combining ABA with rosiglitazone showed significant synergistic activity in downmodulating macrophage accumulation in WAT and in increasing macrophage PPAR γ activity.

Research Design and Methods

Mice and Dietary Treatments

Twelve-fifteen week-old BKS.Cg-+$Lepr^{db}$/+$Lepr^{db}$/OlaHsd (db/db) mice were housed at the animal facilities at Virginia Polytechnic Institute and State University in a room maintained at 75° F., with a 12:12 h light-dark cycle starting from 6:00 AM. All experimental procedures were approved by the Institutional Animal Care and Use Committee of Virginia Polytechnic Institute and State University and met or exceeded requirements of the Public Health Service, National Institutes of Health and the Animal Welfare Act.

Mice (n=40) were fed one of six experimental diets: a control high-fat diet (control), a high-fat diet containing low dose rosiglitazone maleate ($Ros^{lo}$, 10 mg/kg diet), or a high-fat diet containing a high dose of rosiglitazone maleate ($Ros^{hi}$, 70 mg/kg diet), each with or without all racemic ABA (100 mg/kg, Sigma Aldrich, St. Louis, Mo.) for 60 days. Mice were weighed and fasting (12 h) blood glucose levels were taken weekly. Blood glucose levels were assessed with an ACCU-CHEK® Glucometer (Roche, Indianapolis, Ind.). An intraperitoneal glucose tolerance test (IPGTT, 1 g glucose/kg body weight) was conducted on fasted mice (12 h) for 0, 30, 90, and 180 minute time points and insulin levels were measured on day 54. On day 60 mice were sacrificed by $CO_2$ narcosis with secondary thoracotomy. Abdominal WAT, inguinal subcutaneous WAT, and liver were then excised and weighed. Abdominal and subcutaneous WAT were then digested and fractionated.

Digestion of White Adipose Tissue

Abdominal and inguinal subcutaneous WAT was excised, weighed, minced into small <10 mg pieces and placed into digestion media (1×HBSS (Mediatech, Herndon, Va.) supplemented with 2.5% HEPES (Mediatech) and 10% fetal bovine serum containing type II collagenase (0.2%, Sigma-Aldrich). Samples were incubated in a 37° C. incubator for 30 minutes, filtered through a 100 µm nylon cell strainer to remove undigested particles, and centrifuged at 4° C. at 1000×g for 10 minutes. The pellet, consisting of stromal vascular cells (SVCs), was washed with 1×HBSS and centrifuged at 4° C. at 1000×g for 10 minutes. The supernatant was discarded and erythrocytes were lysed by incubating the SVCs in 2 mL erythrocyte lysis buffer for 2 minutes before stopping the reaction with 9 mL 1×PBS. Cells were then respun at 4° C. at 1000×g for 10 minutes, suspended in 1 ml of 1×PBS, and counted with a Coulter Counter (Beckman Coulter, Fullerton, Calif.).

Flow Cytometry

For immunophenotyping SVCs were seeded into 96-well plates (Costar) at $2 \times 10^5$ cell/well. For whole blood 10 µL of each sample was added per well. After an initial 20 minute incubation with FcBlock (20 flg/ml; BD Biosciences-Pharmingen) to inhibit non-specific binding, cells were washed in PBS containing 5% serum and 0.09% sodium azide (FACS buffer) and stained with primary anti-mouse antibodies F4/80 PE-Cy5 (ebioscience, San Diego, Calif.), CD11b Alexa-fluor 700 (ebioscience), CD4 Alexa-Flour 700 (ebioscience), CD25 APC (BD), FoxP3 PE (ebioscience), or anti-human CCR2PE (R&D systems, Minneapolis, Minn.) as previously shown [52]. Flow results were computed with a BD LSR II flow cytometer and data analyses was performed with FACS Diva software (BD).

LPS Treatment of Stromal Vascular Cells

Isolated cells from the stromal vascular fraction (SVF) of WAT from high-fat fed db/db mice were enumerated and seeded into 24-well plates at $2 \times 10^6$ cells/well. Cells were then treated for 6 hrs at 37° C. with LPS (100 ng/mL) in addition to ABA (10 µM), Ros (1 µM), ABA and Ros, or vehicle alone (DMSO). After incubation cells were harvested with RLT lysis buffer and stored in −80° C. for RNA isolation and gene expression analyses.

Real-Time Quantitative PCR

Total RNA was isolated from adipose tissue using the RNeasy Lipid Mini Kit (Qiagen) and from cells using the RNeasy Mini Kit (Qiagen) according to the manufacturer's instructions. Total RNA was used to generate complementary DNA (cDNA) template using the qScript cDNA Synthesis Kit (Quanta Biosciences, Gaithersburg, Md.). The total reaction volume was 20 µL with the reaction incubated as follows in an MJ MiniCycler: 5 minutes at 25° C., 30 minutes at 52° C., 5 minutes at 85° C., hold at 4° C. Each gene amplicon was purified with the MiniElute PCR Purification Kit (Qiagen) and quantitated on an agarose gel by using a DNA mass ladder (Promega). These purified amplicons were used to optimize real-time PCR conditions and to generate standard curves in the real-time PCR assay. Primer concentrations and annealing temperatures were optimized for the iCycler iQ system (Bio-Rad) for each set of primers using the system's gradient protocol. PCR efficiencies were maintained between 92 and 105% and correlation coefficients above 0.98 for each primer set during optimization and also during the real-time PCR of sample DNA as previously shown [46,52,53].

Complementary DNA (cDNA) concentrations for genes of interest were examined by real-time quantitative PCR using an iCycler IQ System and Sybr Green PCR master mix (Applied Biosystems, Foster City, Calif.). A standard curve was generated for each gene using 10-fold dilutions of purified amplicons starting at 5 pg of cDNA and used later to calculate the starting amount of target cDNA in the unknowns. SYBR green I is a general double-stranded DNA intercalating dye and, therefore, may detect nonspecific products and primer/dimers in addition to the amplicon of interest. In order to determine the number of products synthesized during the real-time PCR, a melting curve analysis was performed on each product. Real-time PCR was used to measure the starting amount of nucleic acid of each unknown sample of cDNA on the same 96-well plate. Results are presented as starting quantity of target cDNA (picograms) per microgram of total RNA.

Transfections and PPAR γ Reporter Activity Assay

A pCMX.PPAR γ expression plasmid and a pTKPPRE3x luciferase reporter plasmid driven by the PPRE-containing Acyl-CoA oxidase promoter (kindly provided by Dr. R M. Evans, The Salk Institute, San Diego, Calif.) were purified using Qiagen's Maxi kit (Valencia, Calif.). 3T3-L1 pre-adipocytes and RAW 264.67 macrophages were grown in 25 mm² flasks in high glucose DMEM (Hyclone) containing 10% fetal bovine serum (FBS) until 60-70% confluence. Cells were co-transfected in the 25 mm² with 1.5 µg plasmid DNA and 25 ng of pRL reporter control using F-2 transfection reagents (Targeting Systems, Santee, Calif.) according to the manufacturer's protocol. After 24 hours, transfected cells were split from flasks with trypsin IX (0.25%, Hyclone), enumerated with a cell counter (Coulter Counter, Beckman Coulter), and seeded into white, opaque 96-well plates (BD) at a concentration of 20,000 cells/well. Cells were then treated in replicates of 8 with vehicle (DMSO), rosiglitazone (1 or 10 µM; Cayman Chemicals, Arm Arbor, Mich.), or ABA (10 µM; Sigma) with and without 2'5' dideoxyadenosine (10 µM; Sigma) and 14-22 myristolated PKA inhibitor fragment (PKAi, 30 µM; Sigma). Cells were placed in a 37° C. incubator with 5% $CO_2$ for 6 hours or 24 hours for 3T3-L1 and RAW 264.7, respectively, and were then harvested in reporter lysis reagent. Luciferase activity, normalized to pRL activity in the cell extracts was determined by using the Dual Luciferase II reporter assay system (Promega, Madison, Wis.) using a Modulus 96-well luminometer (Turner Biosystems, Sunnyvale, Calif.). All values were normalized to control wells to calculate relative luciferase activity.

Statistical Analyses

Data were analyzed as a completely randomized design. To determine the statistical significance of the model, analysis of variance (ANOVA) was performed using the general linear model procedure of Statistical Analysis Software (SAS), and probability value $(P)<0.05$ was considered to be significant. When the model was significant, ANOVA was followed by Fisher's Protected Least Significant Difference multiple comparison method.

Results

Effect of Dietary ABA and Rosiglitazone on Obese Db/Db Mice

Db/db mice were fed rosiglitazone at three different concentrations (0, 10, 70 mg/kg diet) with and without ABA (100 mg/kg diet). Both the low- and high-dose rosiglitazone treatments significantly increased the body weights of the mice during the 60-day dietary intervention (Table 1). There was significant edema in the interscapular region in mice fed $Ros^{hi}$ that was not present in the other groups (data not shown).

At day 60 weights of abdominal visceral white adipose tissue (Ab. WAT), inguinal subcutaneous white adipose tissue (SCAT), and livers among the different dietary treatments were compared. ABA and $Ros^{hi}$ significantly and independently reduced Ab. WAT as percent body weight, and there was little affect on inguinal SCAT weight. Liver weights were significantly increased by low dose Ros (Table 1).

TABLE 1

Effect of rosiglitazone and abscisic acid (ABA) combination treatment on body and organ weights.[a,b,c]

| Diet | Initial body weight (g) | Final body weight (g) | Ab. WAT % Body Weight | Sc. WAT % Body Weight | Liver % Body Weight |
|---|---|---|---|---|---|
| No ABA | | | | | |
| Control | 42.6 ± 3.2 | 49.6 ± 1.8$^a$ | 7.2 ± 0.61$^c$ | 2.4 ± 0.48 | 6.2 ± 0.51$^a$ |
| Roslo | 42.0 ± 4.5 | 56.4 ± 2.4$^{bc}$ | 6.7 ± 0.61$^{bc}$ | 2.4 ± 0.43 | 9.2 ± 0.51$^b$ |
| Roshi | 40.6 ± 4.5 | 64.4 ± 2.4$^d$ | 4.6 ± 0.61$^a$ | 3.2 ± 0.43 | 6.7 ± 2.3$^a$ |
| With ABA | | | | | |
| Control | 41.3 ± 4.5 | 53.0 ± 2.7$^{ab}$ | 4.7 ± 0.68$^a$ | 2.8 ± 0.48 | 6.7 ± 0.56$^a$ |
| Roslo | 41.1 ± 4.5 | 51.6 ± 2.4$^{ab}$ | 5.4 ± 0.61$^{ab}$ | 2.6 ± 0.43 | 9.3 ± 0.51$^b$ |
| Roshi | 39.7 ± 4.5 | 62.6 ± 2.4$^{cd}$ | 4.5 ± 0.61$^a$ | 3.5 ± 0.43 | 6.7 ± 51$^a$ |
| P-value for rosiglitazone | 0.94 | <0.0001 | 0.03 | 0.11 | <0.0001 |
| P-value for ABA | 0.70 | 0.59 | 0.02 | 0.46 | 0.77 |
| P-value for interaction | 0.99 | 0.23 | 0.18 | 0.98 | 0.81 |

$^a$Organs were excised and weighed on day 60 of experiment.
$^b$Least squares means values in a column with a pound sign are significantly different (P < 0.05).
$^c$P-value of main effects of rosiglitgazone treatments, ABA, and rosiglitazone and ABA combinations during the 60-day period. Data were analysed as a completely randomized design.

Effect of ABA and rosiglitazone on glucose tolerance and fasting insulin

On day 42 of the dietary intervention an intraperitoneal glucose tolerance test (IPGTT) was performed, and insulin levels were assessed at the end of the study. All treatments, regardless of using ABA, Ros or both, significantly improved glucose tolerance relative to the control diet, though there were no significant effects resulting from a synergism between ABA and rosiglitazone on glucose tolerance. Dietary ABA supplementation significantly reduced fasting insulin levels (P=0.04).

Figure 6:
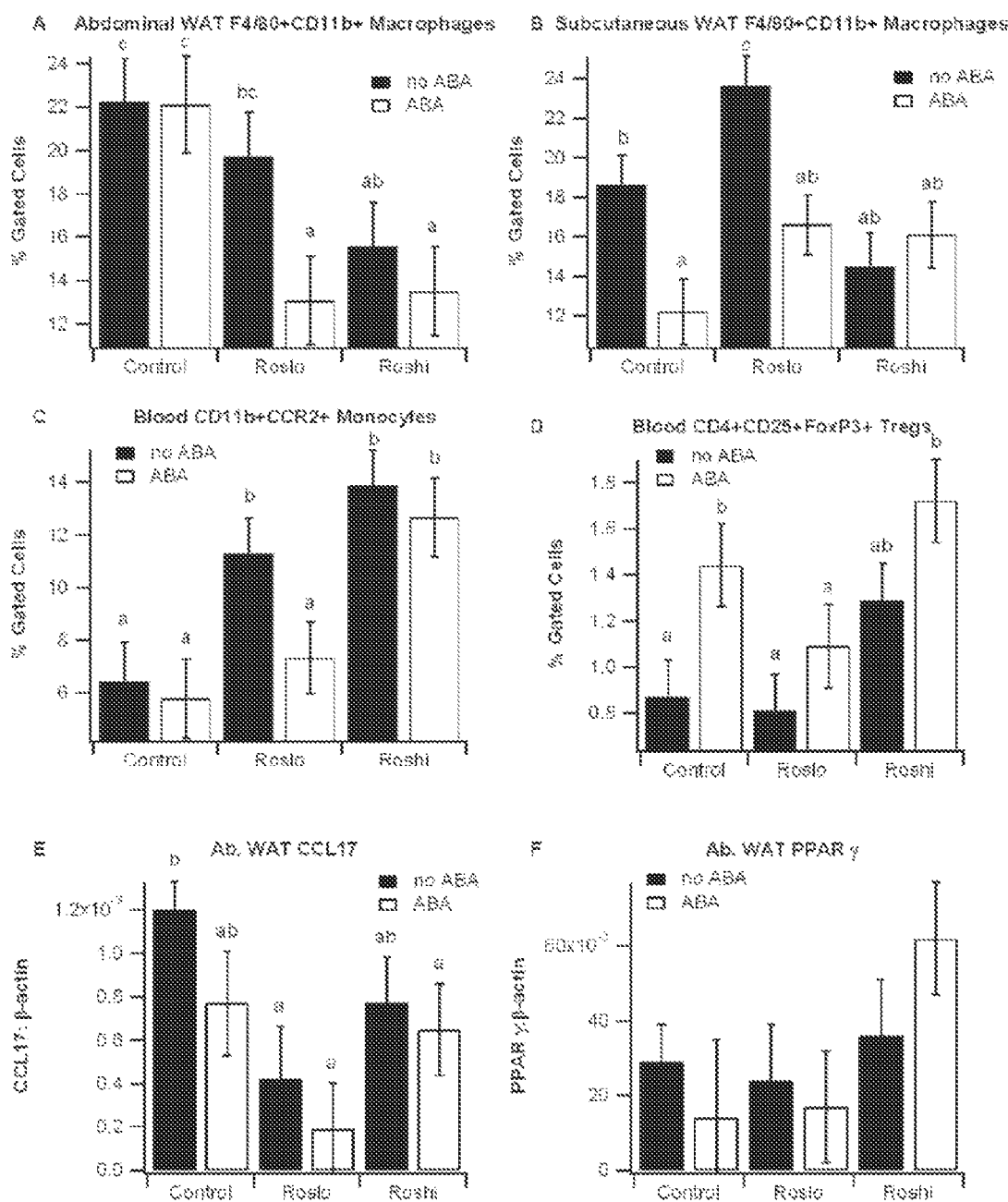
FIG. 6 shows the effect of abscisic acid (ABA) and rosiglitazone (Ros) on immune cell infiltration. Obese db/db mice were fed high-fat diets containing 0, 15, or 70 mg/kg diet rosiglitazone maleate (control, $Ros^{lo}$, and $Ros^{hi}$, respectively) with and without racemic ABA (100 mg/kg diet). On day 60 the percent of F4/80+CD11b+ in the stromal vascular fractions of abdominal white adipose tissue (Ab. WAT) (A) and subcutaneous WAT (B) were assessed by flow cytometry. The percent of CD11b+CCR2+ monocytes (C) and CD4+CD25+ FoxP3+ Tregs (D) in blood were assessed in whole blood. The expressions of the M1 marker CCL17 (E) and peroxisome proliferator activated receptor γ (PPAR γ) (F) in Ab. WAT were calculated as a ratio to the housekeeping gene f3-actin. Data are represented as mean±standard error. Points with different subscripts are significantly different from each other (P<0.05).

Effect of ABA and Rosiglitazone on Macrophage Infiltration into Adipose Tissue and Blood Immune Cells To determine the effect of ABA and Ros on obesity-related inflammation F4/80$^+$CD11b$^+$ macrophage migration into WAT was assessed with flow cytometry and performed gene expression analyses. Independently the ABA and Ros$^{lo}$ treatments had little effect on macrophage infiltration into Ab. WAT, though there was a significant reduction in ATM infiltration when Ros$^{lo}$ was administered in combination with ABA relative to the control diet (FIG. 6). ABA significantly reduced ATM infiltration in SCAT in mice fed the control and Ros$^{lo}$ diets. There was no added benefit in macrophage infiltration by adding ABA to ROS$^{hi}$. Ros significantly reduced expression of the M1 marker CCL17, and the combination of ABA and Ros$^{hi}$ increased numerically, but not significantly, PPAR γ mRNA levels (FIG. 6).

Given that tissue macrophages are repopulated in part by infiltration of bone marrow-derived blood monocytes, the effect of the ABA and Ros dietary combinations on blood immune cells populations was also examined. It was found that Ros significantly and dose-dependently increased blood CCR2$^+$CD11b$^+$ monocyte levels whereas ABA mitigated the Ros$^{lo}$-induced increase and increased the percentages of blood regulatory T cells (Tregs) independently of Ros.

ABA and Rosiglitazone Effects on LPS-Treated SVCs

SVCs from high-fat fed db/db mice were isolated and treated with LPS (100 ng/mL) with and without ABA (10 μM), rosiglitazone (1 μM), and their combination. After a 6-h treatment period a significant increase in PPAR γ expression was observed only in SVCs treated with both ABA and Ros.

Figure 7:
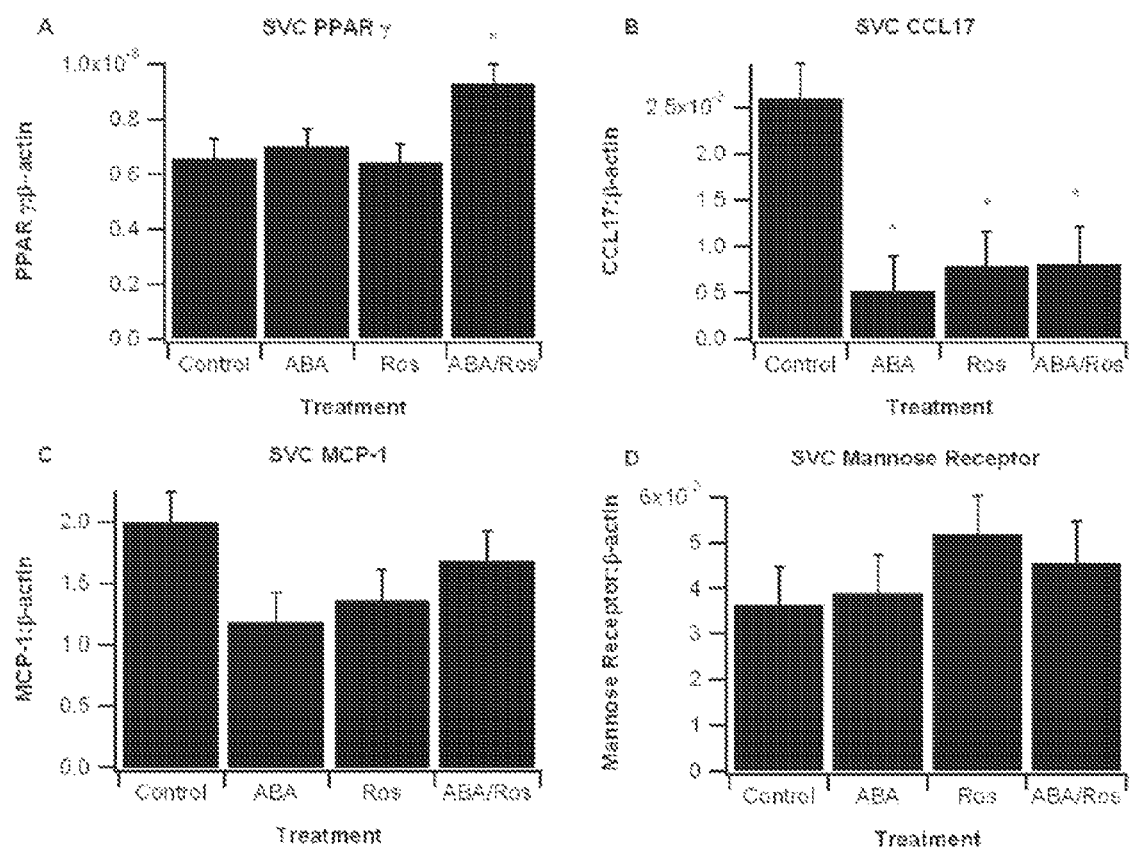
FIG. 7 shows the effect of abscisic acid (ABA) and rosiglitazone combination on gene expression in lipopolysaccharide (LPS)-treated stromal vascular cells (SVCs). SVCs from abdominal white adipose tissue were isolated from db/db mice fed high-fat control diet for 60 days. Cells were seeded into 24-well plates at 1×106 cells/well and treated with LPS (100 ng/mL) with and without ABA (10 μM), Ros (1 μM), or ABA and Ros (ABA/Ros). The relative expressions of genes peroxisome proliferator activated receptor γ (PPAR γ) (A), CCL17 (B), monocyte chemoattractant protein 1 (MCP-1) (C), and mannose receptor (D) were calculated as a ratio to the housekeeping gene β-actin. Data are represented as mean±standard error. Points with an asterisk are significantly different the control treatment (P<0.05).

The M1 marker CCL17 was significantly reduced and all treatments and there were also a numerical reduction in MCP-1 (CCL2, P=0.12). Expression of the mannose receptor, an M2 marker, did not significantly differ among treatments (FIG. 7).

ABA-Induced PPAR γ Activation is Inhibited by cAMP/PKA Inhibition

Figure 8:
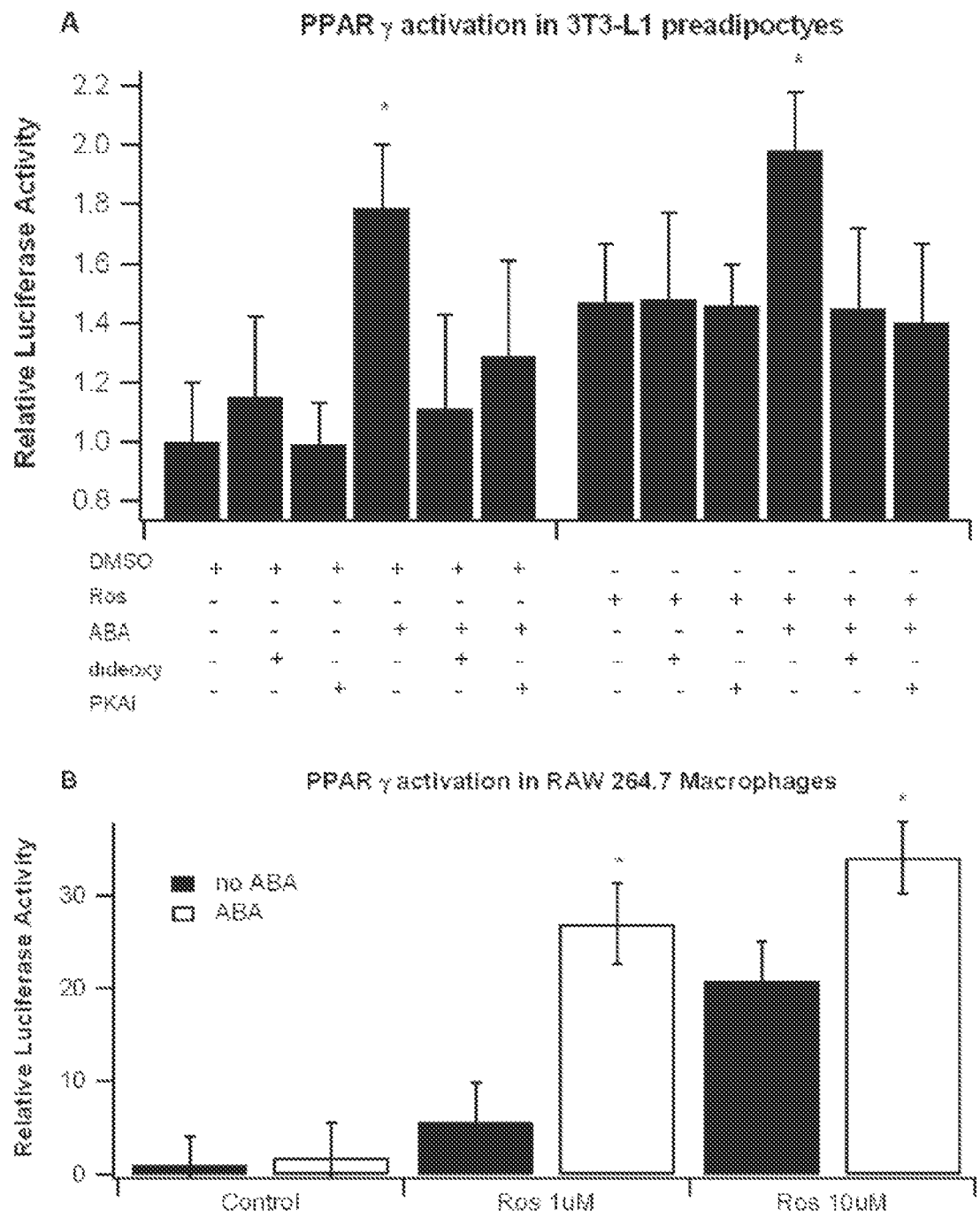
FIG. 8 shows the effect of abscisic acid (ABA) and rosiglitazone (Ros) combination on PPAR γ transactivation. 3T3-L1 preadipocytes (A) and RAW 264.7 macrophages (B) were transfected with a pTK.PPRE3x luciferase reporter plasmid driven by the PPRE containing Acyl-CoA oxidase promoter. For 3T3-L1 preadipocytes cells were treated for 6-h with vehicle (DMSO) or Ros (1 μM) with ABA (10 μM), the cAMP-inhibitor 2'5' dideoxyadenosine (dideoxy, 10 μM), or 14-22 myristolated PKA inhibitor fragment (PKAi, 30 μM). For RAW 264.7 macrophage cells were treated for 24-h with ABA (10 μM), Ros (1 or 10 μM), or their combination. Luciferase activity was normalized to pRL activity in the cell extracts and relative luciferase activity was calculated a ratio of the activity in the treatment wells to control wells. Data are represented as mean±standard error. Points with an asterisk indicate that a treatment is significantly different from its respective 'without ABA' control (P<0.05).

To determine whether ABA-induced activation of PPAR γ is dependent on cAMP/PKA signaling, 3T3-L1 preadipocytes were treated for 6 hrs with or without Ros (1 μM) and ABA (10 μM), 2'5'-dideoxyadenosine (10 μM), and 14-22 myristoylated PKA inhibitor fragment (PKAi, 30 μM). Both ABA and Ros increased PPAR γ activity after the 6-hr treatment, and there was an added benefit from combining the two treatments. Addition of either the cAMP-specific or PKA-specific inhibitor prevented only ABA-induced PPAR γ activation with no effect on Ros-induced PPAR γ activation (FIG. 8A).

The affect of combining ABA with Ros in RAW 264.7 macrophages was also assessed. In this cell line ABA and Ros acted in a synergistic manner, significantly increasing PPAR γ activation (FIG. 8B).

Discussion

ABA is an endogenously produced isoprenoid phytohormone which, when supplemented into the diet, has shown to be effective in preventing obesity-related insulin resistance and inflammation in overweight and obese mice [44]. It has previously been demonstrated that ABA activates PPAR γ in vitro and that its full anti-diabetic effects are dependent on presence of immune cell PPAR γ [44,46]. There are also studies which show that ABA can function through a cAMP/PKA-dependent mechanism [49], and this system has also been shown to positively upregulate PPAR γ [51] by increasing the affinity of PPAR γ for endogenous and synthetic ligands. Previous studies had shown that ABA could be used preventively to suppress inflammation and improve glucose tolerance [44,46]. The main objective of this study was to assess ABA's therapeutic efficacy against diabetes and inflammation alone or in combination with the synthetic PPAR γ ligand rosiglitazone. In contrast to previous ABA studies designed with a focus on prevention and that accordingly used healthy mice at the beginning of the study, this project used mice with pre-established obesity and diabetes, thereby examining for the first time dietary ABA's therapeutic efficacy in diabetes and inflammation.

Obese db/db mice were fed high-fat diets containing rosiglitazone maleate (0, 15, 70 mg/kg) with and without racemic ABA (100 mg/kg) for 60 days. In total, the body and tissue weights showed no enhanced affect from the combined ABA and Ros treatments. It was observed that Ros at both doses significantly increased body weights, and excessive fluid retention in the interscapular region was noted in both of the groups fed Ros$^{hi}$. Both doses of rosiglitazone increased liver weight, and only Ros$^{hi}$ increased inguinal SCAT weight. The finding that Ros-treatment augments liver weight is consistent with previous findings from transgenic obese mice [54], and difference in SCAT between the two groups may account for why there appeared to be more lipid deposition in the Ros$^{lo}$ livers. In contrast to the Ros treatments, ABA did not affect liver weight and independently decreased Ab. WAT mass, suggesting that the decrease in Ab.WAT mass by ABA was PPAR γ-independent.

Obesity is associated with low-grade systemic inflammation, but it has only been in the past five years when it was discovered that macrophages playa major role in its development [55,56]. Macrophages are essential components of the innate immune system that contribute to fighting infections but they are also involved in the genesis of chronic diseases such as diabetes, obesity and atherosclerosis. Obesity and overweight are associated with macrophage infiltration into adipose tissue [52] and a phenotypic switch from an M2 anti-inflammatory phenotype to an M1, pro-inflammatory phenotype [57,58]. Interestingly, significantly enhanced benefits were found from the ABA/Ros combination therapy in regard to macrophage infiltration of visceral and subcutaneous adipose tissue. More specifically, ABA in combination with Ros$^{lo}$ was significantly more effective than either treatment alone in reducing the accumulation of ATMs in the visceral abdominal adipose tissue depot, suggesting a synergistic effect between ABA and Ros$^{lo}$. Additionally, ABA mitigated an increase in adipose tissue macrophages induced by the Ros$^{lo}$ treatment in subcutaneous adipose tissue. In line with these findings, a synergistic enhancement of PPAR γ activation was observed in ABA/Ros treated RAW 264.7 macrophages.

It was also found that ABA independently increases Tregs in the blood of db/db mice. Tregs play an important role in regulating the activation and proliferation of CD4+ lymphocytes, and the obesity-induced increases in circulating leptin and interleukin-6 (1L-6) is thought to contribute to decreased Treg function [59]. In two models of chronic inflammation, the obesity and experimentally-induced colitis model, it has been shown that hepatic Tregs are decreased when compared to healthy control mice [60]. Given the central role of Tregs as down-regulators of inflammation, the maintenance of this population by ABA may account, in part, for its anti-inflammatory effects.

To gain a better understanding of the individual and combined affects of ABA and Ros, SVCs from the WAT of high-fat fed db/db mice were isolated, treated with LPS for 6 hr, and assessed gene expression. The combination treatment, but not ABA or Ros alone, significantly increased PPAR γ expression. TZDs have been shown to differentially increase or decrease PPAR γ expression while still enhancing PPAR γ activity [51,61]. Expression of M1 markers were reduced by ABA, Ros and ABA/Ros treatment, suggesting that both ABA and Ros can down-modulate M1 polarization or reduce macrophage pro-inflammatory production in SVCs. PPAR γ activation is involved in the priming of monocytes towards the alternatively activated, anti-inflammatory phenotype [62,63]. Significant changes in the M2 marker mannose receptor in the SVF were not observed, though this was perhaps due to a limited number of monocytes in the SVF.

Bruzzone et al recently showed that ABA significantly enhances insulin secretion in INS-1 and MIN-6 pancreatic cells through a cAMP-dependent mechanism [49]. Wantanbe has also linked the cAMP/PKA pathway to enhancing PPAR γ activity [51]. Here it is shown that ABA decreases fasting insulin levels independent of TZD and also that the ABA-induced activation of PPAR γ in 3T3-L1 preadipocytes is inhibited by both cAMP/PKA inhibitors used. These findings suggest that ABA's effects on PPAR γ may be initiated though a membrane mechanism involving a G protein-coupled receptor, increased intracellular cAMP levels and PKA activation.

In conclusion, the findings show that ABA can effectively treat glucose tolerance and obesity-related inflammation in mice with pre-existing obesity. Here it is also shown that its in vivo effects differ from that of the TZDs and that combination of low-dose TZD with ABA may be more effective and safer than either of the two individually in ameliorating chronic inflammation.

It will be apparent to those skilled in the art that various modifications and variations can be made in the practice of the present invention without departing from the scope of the invention. Other embodiments of the invention will be apparent to those skilled in the art from consideration of the specification and practice of the invention. It is intended that the specification and examples be considered as exemplary only, with a true scope and spirit of the invention being indicated by the following claims.

REFERENCES

1. Ogden C L, Carroll M D, Curtin L R, McDowell M A, Tabak C J, Flegal K M. Prevalence of overweight and obesity in the United States, 1999-2004. JAMA 2006; 295: 1549-55.
2. Clinical Guidelines on the Identification, Evaluation, and Treatment of Overweight and Obesity in Adults—The Evidence Report. National Institutes of Health. Obes Res 1998; 6 Suppl 2:51 S-209S.
3. Dietz W H. Health consequences of obesity in youth: childhood predictors of adult disease. Pediatrics 1998; 101:518-25.
4. Hotamisligil G S. Role of endoplasmic reticulum stress and c-Jun NH2-terminal kinase pathways in inflammation and origin of obesity and diabetes. Diabetes 2005; 54 Suppl 2:S73-8.
5. Tuncman G, Hirosumi J, Solinas G, Chang L, Karin M, Hotamisligil G S. Functional in vivo interactions between JNK1 and JNK2 isoforms in obesity and insulin resistance. Proc Natl Acad Sci USA 2006; 103:10741-6.
6. Yuan M, Konstantopoulos N, Lee J, et al. Reversal of obesity- and diet-induced insulin resistance with salicylates or targeted disruption of Ikkbeta. Science 2001; 293: 1673-7.
7. Arkan M C, Hevener A L, Greten F R, et al. IKK-beta links inflammation to obesity induced insulin resistance. Nat Med 2005; 11:191-8.
8. Davis J E, Gabler N K, Walker-Daniels J, Spurlock M E. Tlr-4 deficiency selectively protects against obesity induced by diets high in saturated fat. Obesity (Silver Spring) 2008; 16:1248-55.

9. Lehmann J M, Moore L B, Smith-Oliver T A, Wilkison W O, Willson T M, Kliewer S A. An anti-diabetic thiazolidinedione is a high affinity ligand for peroxisome proliferator-activated receptor gamma (PPAR gamma). J Biol Chem 1995; 270:12953-6.
10. Yamauchi T, Kadowaki T. [The molecular mechanisms by which PPAR gamma/RXR inhibitors improve insulin resistance]. Nippon Rinsho 2001; 59:2245-54.
11. Bays H E, Gonzalez-Campoy J M, Bray G A, et al. Pathogenic potential of adipose tissue and metabolic consequences of adipocyte hypertrophy and increased visceral adiposity. Expert Rev Cardiovasc Ther 2008; 6:343-68.
12. Weisberg S P, McCann D, Desai M, Rosenbaum M, Leibel R L, Ferrante A W, Jr. Obesity is associated with macrophage accumulation in adipose tissue. J Clin Invest 2003; 112:1796-808.
13. Pascual G, Fong A L, Ogawa S, et al. A SUMOylation-dependent pathway mediates transrepression of inflammatory response genes by PPAR-gamma. Nature 2005; 437:759-63.
14. Tanaka T, Fukunaga Y, Itoh H, et al. Therapeutic potential of thiazolidinediones in activation of peroxisome proliferator-activated receptor gamma for monocyte recruitment and endothelial regeneration. Eur J Pharmacol 2005; 508:255-65.
15. Jennewein C, Kuhn A M, Schmidt M V, et al. Sumoylation of peroxisome proliferatoractivated receptor gamma by apoptotic cells prevents lipopolysaccharide-induced NCoR removal from kappaB binding sites mediating transrepression of proinflammatory cytokines. J Immunol 2008; 181:5646-52.
16. Blanquicett C, Roman J, Hart C M. Thiazolidinediones as anti-cancer agents. Cancer Ther 2008; 6:25-34.
17. Mestre L, Docagne F, Correa F, et al. A cannabinoid agonist interferes with the progression of a chronic model of multiple sclerosis by downregulating adhesion molecules. Mol Cell Neurosci 2008.
18. Serghides L, Kain K C. Peroxisome proliferator-activated receptor gamma-retinoid X receptor agonists increase CD36-dependent phagocytosis of *Plasmodium falciparum*-parasitized erythrocytes and decrease malaria-induced TNF-alpha secretion by monocytes/macrophages. J Immunol 2001; 166:6742-8.
19. Barna B P, Culver D A, Abraham S, et al. Depressed peroxisome proliferator-activated receptor gamma (PPar-gamma) is indicative of severe pulmonary sarcoidosis: possible involvement of interferon gamma (IFN-gamma). Sarcoidosis Vasc Diffuse Lung Dis 2006; 23:93-100.
20. Serhan C N, Devchand P R. Novel anti-inflammatory targets for asthma. A role for PPARgamma? Am J Respir Cell Mol Biol 2001; 24:658-61.
21. Diab A, Deng C, Smith J D, et al. Peroxisome proliferator-activated receptor-gamma agonist 15-deoxy-Delta(12,14)-prostaglandin J(2) ameliorates experimental autoimmune encephalomyelitis. J Immunol 2002; 168:2508-15.
22. Diab A, Hussain R Z, Lovett-Racke A E, Chavis J A, Drew P D, Racke M K. Ligands for the peroxisome proliferator-activated receptor-gamma and the retinoid X receptor exert additive anti-inflammatory effects on experimental autoimmune encephalomyelitis. J Neuroimmunol 2004; 148:116-26.
23. Raikwar H P, Muthian G, Rajasingh J, Johnson C, Bright J J. PPARgamma antagonists exacerbate neural antigen-specific Th1 response and experimental allergic encephalomyelitis. J Neuroimmunol 2005; 167:99-107.
24. Storer P D, Xu J, Chavis J, Drew P D. Peroxisome proliferator-activated receptor-gamma agonists inhibit the activation of microglia and astrocytes: implications for multiple sclerosis. J Neuroimmunol 2005; 161:113-22.
25. Hontecillas R, Bassaganya-Riera J. Peroxisome proliferator-activated receptor gamma is required for regulatory CD4+ T cell-mediated protection against colitis. J Immunol 2007; 178:2940-9.
26. Ramakers J D, Verstege M I, Thuijls G, Te Velde A A, Mensink R P, Plat J. The PPARgamma agonist rosiglitazone impairs colonic inflammation in mice with experimental colitis. J Clin Immunol 2007; 27:275-83.
27. Lewis J D, Lichtenstein G R, Stein R B, et al. An open-label trial of the PPAR-gamma ligand rosiglitazone for active ulcerative colitis. Am J Gastroenterol 2001; 96:3323-8.
28. Kobayashi T, Notoya K, Naito T, et al. Pioglitazone, a peroxisome proliferator-activated receptor gamma agonist, reduces the progression of experimental osteoarthritis in guinea pigs. Arthritis Rheum 2005; 52:479-87.
29. Demerjian M, Man M Q, Choi E H, et al. Topical treatment with thiazolidinediones, activators of peroxisome proliferator-activated receptor-gamma, normalizes epidermal homeostasis in a murine hyperproliferative disease model. Exp Dermatol 2006; 15:154-60.
30. Bolzano K. [Biguanides: reasons for withdrawal of drugs and remaining indications]. Acta Med Austriaca 1978; 5:85-8.
31. d'Uscio L V, Baker T A, Mantilla C B, et al. Mechanism of endothelial dysfunction in apolipoprotein E-deficient mice. Arterioscler Thromb Vasc Biol 2001; 21:1017-22.
32. Hoist J J. Treatment of type 2 diabetes mellitus with agonists of the GLP-1 receptor or DPP-IV inhibitors. Expert Opin Emerg Drugs 2004; 9:155-66.
33. Drucker D J, Philippe J, Mojsov S, Chick W L, Habener J F. Glucagon-like peptide I stimulates insulin gene expression and increases cyclic AMP levels in a rat islet cell line. Proc Natl Acad Sci USA 1987; 84:3434-8.
34. Klett C, Nobiling R, Gierschik P, Hackenthal E. Angiotensin II stimulates the synthesis of angiotensinogen in hepatocytes by inhibiting adenylylcyclase activity and stabilizing angiotensinogen mRNA. J Biol Chem 1993; 268:25095-107.
35. Krumenacker J S, Katsuki S, Kots A, Murad F. Differential expression of genes involved in cGMP-dependent nitric oxide signaling in murine embryonic stem (ES) cells and ES cell derived cardiomyocytes. Nitric Oxide 2006; 14:1-11.
36. Murad F. Shattuck Lecture. Nitric oxide and cyclic GMP in cell signaling and drug development. N Engl J Med 2006; 355:2003-11.
37. Hanefeld M, Marx N, Pfutzner A, et al. Anti-inflammatory effects of pioglitazone and/or simvastatin in high cardiovascular risk patients with elevated high sensitivity C-reactive protein: the PIOSTAT Study. J Am Coll Cardiol 2007; 49:290-7.
38. Martin G, Duez H, Blanquart C, et al. Statin-induced inhibition of the Rho-signaling pathway activates PPARalpha and induces HDL apoA-I. J Clin Invest 2001; 107:1423-32.
39. Ye Y, Nishi S P, Manickavasagam S, et al. Activation of peroxisome proliferatoractivated receptor-gamma (PPAR-gamma) by atorvastatin is mediated by 15-deoxy-delta-12,14-PGJ2. Prostaglandins Other Lipid Mediat 2007; 84:43-53.
40. Singh Ahuja H, Liu S, Crombie D L, et al. Differential effects of rexinoids and thiazolidinediones on metabolic gene expression in diabetic rodents. Mol Pharmacol 2001; 59:765-73.

41. Altucci L, Rossin A, Hirsch O, et al. Rexinoid-triggered differentiation and tumorselective apoptosis of acute myeloid leukemia by protein kinase A-mediated desubordination of retinoid X receptor. Cancer Res 2005; 65:8754-65.
42. Dragnev K H, Petty W J, Ma Y, Rigas J R, Dmitrovsky E. Nonclassical retinoids and lung carcinogenesis. Clin Lung Cancer 2005; 6:237-44.
43. Finkelstein E A, Trogdon J G, Cohen J W, Dietz W. Annual medical spending attributable to obesity: Payer- and service-specific estimates. Health Aff (Millwood) 2009.
44. Guri A J, Hontecillas R, Si H, Liu D, Bassaganya-Riera 1. Dietary abscisic acid ameliorates glucose tolerance and obesity-related inflammation in db/db mice fed high-fat diets. Clin Nutr 2007; 26:107-16.
45. Bruzzone S, Moreschi I, Usai C, et al. Abscisic acid is an endogenous cytokine in human granulocytes with cyclic adp-ribose as second messenger. Proc Natl Acad Sci USA 2007; 104:5759-64.
46. Guri A J, Hontecillas R, Ferrer G, et al. Loss of ppar gamma in immune cells impairs the ability of abscisic acid to improve insulin sensitivity by suppressing monocyte chemoattractant protein-I expression and macrophage infiltration into white adipose tissue. J Nutr Biochem 2008; 19:216-28.
47. Marcy T R, Britton M L, Blevins S M. Second-generation thiazolidinediones and hepatotoxicity. Ann Pharmacother 2004; 38: 1419-23.
48. Nesto R W, Bell D, Bonow R O, et al. Thiazolidinedione use, fluid retention, and congestive heart failure: A consensus statement from the american heart association and american diabetes association. Oct. 7, 2003. Circulation 2003; 108:2941-8.
49. Bruzzone S, Bodrato N, Usai C, et al. Abscisic acid is an endogenous stimulator of insulin release from human pancreatic islets with cyclic adp ribose as second messenger. J Bioi Chem 2008; 283:32188-97.
50. Magnone M, Bruzzone S, Guida L, et al. Abscisic acid released by human monocytes activates monocytes and vascular smooth muscle cell responses involved in atherogenesis. J Bioi Chem 2009
51. Watanabe M, Inukai K, Katagiri H, Awata T, Oka Y, Katayama S. Regulation of ppar gamma transcriptional activity in 3t3-11 adipocytes. Biochem Biophys Res Commun 2003; 300:429-36.
52. Bassaganya-Riera J, Misyak S, Guri A J, Hontecillas R. Ppar gamma is highly expressed in f4/80(hi) adipose tissue macrophages and dampens adipose-tissue inflammation. Cell Immunol 2009
53. Bassaganya-Riera J, Reynolds K, Martino-Catt S, et al. Activation ofppar gamma and delta by conjugated linoleic acid mediates protection from experimental inflammatory bowel disease. Gastroenterology 2004; 127:777-91.
54. Walczak R, Tontonoz P. Pparadigms and pparadoxes: Expanding roles for ppargamma in the control of lipid metabolism. J Lipid Res 2002; 43:177-86.
55. Xu H, Barnes G T, Yang Q, et al. Chronic inflammation in fat plays a crucial role in the development of obesity-related insulin resistance. J Clin Invest 2003; 112:1821-30.
56. Weisberg S P, McCann D, Desai M, Rosenbaum M, Leibel R L, Ferrante A W, Jr. Obesity is associated with macrophage accumulation in adipose tissue. J Clin Invest 2003; 112: 1796-808.
57. Kang K, Reilly S M, Karabacak V, et al. Adipocyte-derived thZ cytokines and myeloid ppardelta regulate macrophage polarization and insulin sensitivity. Cell Metab 2008; 7:485-95.
58. Odegaard J I, Ricardo-Gonzalez R R, Red Eagle A, et al. Alternative m2 activation of kupffer cells by ppardelta ameliorates obesity-induced insulin resistance. Cell Metab 2008; 7:496-507.
59. Hersoug L G, Linneberg A. The link between the epidemics of obesity and allergic diseases: Does obesity induce decreased immune tolerance? Allergy 2007; 62: 1205-13.
60. Bassaganya-Riera J, Ferrera G, Casagrana 0, et al. F4/80hiccr2hi macrophage infiltration into the intra-abdominal fat worsens the severity of experimental ibd in obese mice with dss colitis e-SPEN, the European e-Journal of Clinical Nutrition and Metabolism 2009; 4
61. Suzuki A, Yasuno T, Kojo H, Hirosumi J, Mutoh S, Notsu Y. Alteration in expression profiles of a series of diabetes-related genes in db/db mice following treatment with thiazolidinediones. Jpn J Pharmacol 2000; 84:113-23.
62. Bouhlel M A, Derudas B, Rigamonti E, et al. Ppargamma activation primes human monocytes into alternative m2 macrophages with anti-inflammatory properties. Cell Metab 2007; 6: 137-43.
63. Odegaard J I, Ricardo-Gonzalez R R, Goforth M H, et al. Macrophage-specific ppargamma controls alternative activation and improves insulin resistance. Nature 2007; 447: 1116-20.

The invention claimed is:

1. A method of enhancing the efficacy of a thiazolidinedione (TZD) in increasing peroxisome proliferator-activated receptor γ (PPARγ) activity, said method comprising: administering the TZD in combination with abscisic acid.

2. The method of claim 1, wherein the TZD is rosiglitazone.

* * * * *